US011543646B2

(12) United States Patent
Kirma et al.

(10) Patent No.: US 11,543,646 B2
(45) Date of Patent: Jan. 3, 2023

(54) OPTICAL SYSTEMS FOR MULTI-SENSOR ENDOSCOPES

(71) Applicant: EndoChoice Innovation Center Ltd., Caesarea (IL)

(72) Inventors: Yaniv Kirma, Karcur (IL); Victor Levin, Haifa (IL); Moshe Levi, Ganey Tikva (IL)

(73) Assignee: EndoChoice, Inc., Alpharetta, GA (US)

( * ) Notice: Subject to any disclaimer, the term of this patent is extended or adjusted under 35 U.S.C. 154(b) by 115 days.

(21) Appl. No.: 16/230,728

(22) Filed: Dec. 21, 2018

(65) Prior Publication Data
US 2019/0121118 A1    Apr. 25, 2019

Related U.S. Application Data

(63) Continuation of application No. 15/092,970, filed on Apr. 7, 2016, now Pat. No. 10,203,493, which is a (Continued)

(51) Int. Cl.
*G02B 23/24* (2006.01)
*A61B 1/00* (2006.01)
(Continued)

(52) U.S. Cl.
CPC ........ *G02B 23/243* (2013.01); *A61B 1/00096* (2013.01); *A61B 1/00177* (2013.01);
(Continued)

(58) Field of Classification Search
CPC .......... G02B 23/243; G02B 7/04; G02B 9/60; G02B 13/001; G02B 13/0015; A61B 1/00177; A61B 1/00181; A61B 1/00188
See application file for complete search history.

(56) References Cited

U.S. PATENT DOCUMENTS 3,639,714 A    2/1972  Fujimoto
3,955,064 A    5/1976  Demetrio
(Continued)

FOREIGN PATENT DOCUMENTS

CN    1376443      10/2002
CN    2829646 Y    10/2006
(Continued)

OTHER PUBLICATIONS

Office Action dated Jun. 30, 2016 for U.S. Appl. No. 13/655,120.
(Continued)

*Primary Examiner* — Anh Tuan T Nguyen
*Assistant Examiner* — Jae Woo
(74) *Attorney, Agent, or Firm* — Bookoff McAndrews, PLLC

(57) ABSTRACT

There is provided herein an optical system for a tip section of a multi-sensor endoscope, the system comprising: a front-pointing camera sensor; a front objective lens system; a side-pointing camera sensor; and a side objective lens system, wherein at least one of said front and side objective lens systems comprises a front and a rear sub-systems separated by a stop diaphragm, said front sub-system comprises, in order from the object side, a first front negative lens and a second front positive lens, said rear sub-system comprises, in order from the object side, a first rear positive lens, an achromatic sub-assembly comprising a second rear positive lens and a third rear negative lens, wherein the following condition is satisfied: $f_{(first\ rear\ positive\ lens)} \leq 1.8 f$, where f is the composite focal length of the total lens system and $f_{(first\ rear\ positive\ lens)}$ is the focal length of said first rear positive lens.

10 Claims, 11 Drawing Sheets

Related U.S. Application Data continuation of application No. 13/882,004, filed as application No. PCT/IL2011/000832 on Oct. 27, 2011, now abandoned.

(60) Provisional application No. 61/407,495, filed on Oct. 28, 2010.

(51) Int. Cl.
| | |
|---|---|
| *G02B 13/00* | (2006.01) |
| *G02B 7/04* | (2021.01) |
| *A61B 1/05* | (2006.01) |
| *G02B 13/04* | (2006.01) |
| *G02B 9/60* | (2006.01) |
| *G02B 13/06* | (2006.01) |

(52) U.S. Cl.
CPC ...... *A61B 1/00181* (2013.01); *A61B 1/00188* (2013.01); *A61B 1/05* (2013.01); *G02B 7/04* (2013.01); *G02B 9/60* (2013.01); *G02B 13/001* (2013.01); *G02B 13/005* (2013.01); *G02B 13/0015* (2013.01); *G02B 13/04* (2013.01); *G02B 13/06* (2013.01); *G02B 23/2407* (2013.01); *G02B 23/2461* (2013.01); *G02B 23/2476* (2013.01); *G02B 23/2484* (2013.01)

(56) References Cited

U.S. PATENT DOCUMENTS

| | | | |
|---|---|---|---|
| 4,037,588 A | 7/1977 | Heckele | |
| 4,084,401 A | 4/1978 | Belardi | |
| 4,253,448 A | 3/1981 | Terada | |
| 4,261,345 A | 4/1981 | Yamaguchi | |
| 4,402,313 A | 9/1983 | Yabe | |
| 4,414,608 A | 11/1983 | Furihata | |
| 4,439,030 A | 3/1984 | Ueda | |
| 4,469,090 A | 9/1984 | Konomura | |
| 4,494,549 A | 1/1985 | Namba | |
| 4,522,196 A | 6/1985 | Cunningham | |
| 4,558,691 A * | 12/1985 | Okada | A61B 1/00165 600/117 |
| 4,565,423 A | 1/1986 | Ueda | |
| 4,576,144 A | 3/1986 | Ishii | |
| 4,588,294 A * | 5/1986 | Siegmund | G02B 23/26 356/241.1 |
| 4,590,923 A | 5/1986 | Watanabe | |
| 4,639,772 A * | 1/1987 | Sluyter | H04N 5/2254 348/373 |
| 4,641,635 A | 2/1987 | Yabe | |
| 4,699,463 A | 10/1987 | D'Amelio | |
| 4,708,126 A | 11/1987 | Toda | |
| 4,727,859 A | 3/1988 | Lia | |
| 4,736,732 A | 4/1988 | Shimonaka | |
| 4,736,734 A * | 4/1988 | Matsuura | A61B 1/00188 348/68 |
| 4,753,222 A | 6/1988 | Morishita | |
| 4,764,001 A * | 8/1988 | Yokota | G02B 13/04 359/740 |
| 4,765,313 A * | 8/1988 | Kumakura | A61B 1/00188 600/167 |
| 4,794,913 A | 1/1989 | Shimonaka | |
| 4,801,792 A * | 1/1989 | Yamasita | G02B 5/005 250/205 |
| 4,841,952 A | 6/1989 | Sato | |
| 4,846,154 A | 7/1989 | MacAnally | |
| 4,868,644 A | 9/1989 | Yabe | |
| 4,877,314 A * | 10/1989 | Kanamori | G02B 15/04 359/673 |
| 4,878,485 A | 11/1989 | Adair | |
| 4,888,639 A | 12/1989 | Yabe | |
| 4,902,115 A * | 2/1990 | Takahashi | G02B 5/005 348/335 |
| 4,905,670 A | 3/1990 | Adair | |
| 4,914,521 A | 4/1990 | Adair | |
| 4,974,075 A | 11/1990 | Nakajima | |
| 4,976,522 A * | 12/1990 | Igarashi | G02B 15/177 359/680 |
| 4,982,724 A | 1/1991 | Saito | |
| 4,984,878 A * | 1/1991 | Miyano | G02B 9/34 359/783 |
| 4,998,182 A | 3/1991 | Krauter | |
| 5,056,902 A * | 10/1991 | Chinnock | A61B 34/73 359/503 |
| 5,166,787 A | 11/1992 | Irion | |
| 5,193,525 A | 3/1993 | Silverstein | |
| 5,239,983 A | 8/1993 | Katsurada | |
| 5,296,971 A * | 3/1994 | Mori | G02B 23/243 359/716 |
| 5,299,561 A | 4/1994 | Yoshimoto | |
| 5,305,121 A | 4/1994 | Moll | |
| 5,309,227 A | 5/1994 | Inoue | |
| 5,313,934 A | 5/1994 | Wiita | |
| 5,331,950 A * | 7/1994 | Wood, Sr. | A61B 1/0669 600/109 |
| 5,339,800 A | 8/1994 | Wiita | |
| 5,359,456 A * | 10/1994 | Kikuchi | G02B 9/10 359/654 |
| 5,359,992 A * | 11/1994 | Hori | A61B 1/00188 126/4 |
| 5,380,049 A | 1/1995 | Smowton | |
| 5,398,056 A | 3/1995 | Yabe | |
| 5,408,263 A | 4/1995 | Dolidon | |
| 5,412,478 A | 5/1995 | Ishihara | |
| 5,420,644 A | 5/1995 | Watanabe | |
| 5,432,543 A | 7/1995 | Hasegawa | |
| 5,436,767 A | 7/1995 | Suzuki | |
| 5,447,148 A | 9/1995 | Oneda | |
| 5,452,391 A | 9/1995 | Chou | |
| 5,460,167 A | 10/1995 | Yabe | |
| 5,475,420 A | 12/1995 | Buchin | |
| 5,483,951 A | 1/1996 | Frassica | |
| 5,485,316 A | 1/1996 | Mori | |
| 5,489,256 A | 2/1996 | Adair | |
| 5,507,717 A | 4/1996 | Kura | |
| 5,512,940 A | 4/1996 | Takasugi | |
| 5,515,449 A | 5/1996 | Tsuruoka | |
| 5,518,501 A | 5/1996 | Oneda | |
| 5,518,502 A | 5/1996 | Kaplan | |
| 5,547,455 A | 8/1996 | McKenna | |
| 5,547,457 A * | 8/1996 | Tsuyuki | A61B 1/00096 359/239 |
| 5,550,582 A | 8/1996 | Takasugi | |
| 5,575,757 A * | 11/1996 | Kennedy | A61B 1/00188 348/65 |
| 5,585,840 A | 12/1996 | Watanabe | |
| 5,587,839 A * | 12/1996 | Miyano | G02B 9/34 359/660 |
| 5,589,874 A | 12/1996 | Buchin | |
| 5,592,216 A | 1/1997 | Uehara | |
| 5,605,530 A | 2/1997 | Fischell | |
| 5,609,560 A | 3/1997 | Ichikawa | |
| 5,617,136 A | 4/1997 | Iso | |
| 5,630,782 A | 5/1997 | Adair | |
| 5,653,677 A | 8/1997 | Okada | |
| 5,656,011 A | 8/1997 | Uihlein | |
| 5,662,588 A | 9/1997 | Iida | |
| 5,675,378 A | 10/1997 | Takasugi | |
| 5,679,110 A | 10/1997 | Hamazaki | |
| 5,685,823 A | 11/1997 | Ito | |
| 5,701,155 A | 12/1997 | Wood | |
| 5,702,345 A | 12/1997 | Wood | |
| 5,702,347 A | 12/1997 | Yabe | |
| 5,706,143 A * | 1/1998 | Hipp | G02B 23/2476 126/4 |
| 5,707,344 A | 1/1998 | Nakazawa | |
| 5,716,323 A | 2/1998 | Lee | |
| 5,725,474 A | 3/1998 | Yasui | |
| 5,725,476 A | 3/1998 | Yasui | |
| 5,725,477 A | 3/1998 | Yasui | |
| 5,728,045 A | 3/1998 | Komi | |

(56) References Cited

U.S. PATENT DOCUMENTS

| | | | |
|---|---|---|---|
| 5,751,340 A | 5/1998 | Strobl | |
| 5,764,809 A | 6/1998 | Nomami | |
| 5,777,797 A * | 7/1998 | Miyano | G02B 23/243 |
| | | | 359/660 |
| 5,782,751 A | 7/1998 | Matsuno | |
| 5,793,539 A | 8/1998 | Konno | |
| 5,800,341 A | 9/1998 | McKenna | |
| 5,812,187 A | 9/1998 | Watanabe | |
| 5,830,124 A | 11/1998 | Suzuki | |
| 5,836,894 A | 11/1998 | Sarvazyan | |
| 5,852,511 A | 12/1998 | Tateyama | |
| 5,860,913 A | 1/1999 | Yamaya | |
| 5,870,234 A * | 2/1999 | Ebbesmeier nee Schitthof | |
| | | | G02B 13/06 |
| | | | 359/713 |
| 5,871,439 A | 2/1999 | Takahashi | |
| 5,871,440 A | 2/1999 | Okada | |
| 5,876,326 A | 3/1999 | Takamura | |
| 5,879,284 A | 3/1999 | Tsujita | |
| 5,894,322 A | 4/1999 | Hamano | |
| 5,912,764 A | 6/1999 | Togino | |
| 5,913,817 A | 6/1999 | Lee | |
| 5,914,810 A | 6/1999 | Watts | |
| 5,916,148 A * | 6/1999 | Tsuyuki | G02B 9/34 |
| | | | 600/160 |
| 5,929,901 A | 7/1999 | Adair | |
| 5,930,424 A | 7/1999 | Heimberger | |
| 5,933,275 A | 8/1999 | Igarashi | |
| 5,933,282 A | 8/1999 | Tomioka | |
| 5,936,773 A | 8/1999 | Togino | |
| 5,940,126 A | 8/1999 | Kimura | |
| 5,961,445 A | 10/1999 | Chikama | |
| 5,969,888 A | 10/1999 | Sukekawa | |
| 5,978,161 A * | 11/1999 | Lemke | A61B 1/00188 |
| | | | 359/824 |
| 5,986,693 A | 11/1999 | Adair | |
| 5,989,185 A | 11/1999 | Miyazaki | |
| 5,993,037 A | 11/1999 | Tomioka | |
| 5,995,136 A | 11/1999 | Hattori | |
| 6,009,189 A | 12/1999 | Schaack | |
| 6,025,873 A | 2/2000 | Nishioka | |
| 6,043,839 A | 3/2000 | Adair | |
| 6,069,651 A * | 5/2000 | Tsuyuki | G02B 23/2423 |
| | | | 348/75 |
| 6,069,698 A | 5/2000 | Ozawa | |
| 6,080,104 A | 6/2000 | Ozawa | |
| 6,104,540 A | 8/2000 | Hayakawa | |
| 6,110,127 A | 8/2000 | Suzuki | |
| 6,117,068 A | 9/2000 | Gourley | |
| 6,124,989 A | 9/2000 | Oode | |
| 6,139,175 A | 10/2000 | Tomioka | |
| 6,139,490 A | 10/2000 | Breidenthal | |
| 6,147,808 A | 11/2000 | Togino | |
| 6,163,401 A | 12/2000 | Igarashi | |
| 6,166,858 A | 12/2000 | Togino | |
| 6,181,481 B1 * | 1/2001 | Yamamoto | G02B 9/12 |
| | | | 359/558 |
| 6,184,923 B1 | 2/2001 | Miyazaki | |
| 6,185,046 B1 | 2/2001 | Togino | |
| 6,196,967 B1 | 3/2001 | Lim | |
| 6,201,648 B1 | 3/2001 | Togino | |
| 6,210,322 B1 | 4/2001 | Byrne | |
| 6,211,904 B1 | 4/2001 | Adair | |
| 6,215,517 B1 | 4/2001 | Takahashi | |
| 6,217,500 B1 | 4/2001 | Helseth | |
| 6,245,086 B1 | 6/2001 | Storz | |
| 6,249,391 B1 | 6/2001 | Hayakawa | |
| 6,260,994 B1 | 7/2001 | Matsumoto | |
| 6,261,226 B1 | 7/2001 | McKenna | |
| 6,275,255 B1 | 8/2001 | Adair | |
| 6,295,368 B1 | 9/2001 | Hasegawa | |
| 6,306,082 B1 | 10/2001 | Takahashi | |
| 6,310,642 B1 | 10/2001 | Adair | |
| 6,310,736 B1 | 10/2001 | Togino | |
| 6,315,712 B1 | 11/2001 | Rovegno | |
| 6,322,496 B1 | 11/2001 | Iida | |
| 6,327,094 B1 | 12/2001 | Aoki | |
| 6,327,101 B1 | 12/2001 | Miyano | |
| 6,334,845 B1 | 1/2002 | Higuchi | |
| 6,353,504 B1 | 3/2002 | Yamamoto | |
| 6,375,610 B2 | 4/2002 | Verschuur | |
| 6,387,045 B1 | 5/2002 | Takahashi | |
| 6,398,723 B1 | 6/2002 | Kehr | |
| 6,400,514 B2 | 6/2002 | Minami | |
| 6,409,657 B1 * | 6/2002 | Kawano | A61B 1/00091 |
| | | | 600/127 |
| 6,422,995 B2 | 7/2002 | Akiba | |
| 6,425,857 B1 | 7/2002 | Rudischhauser | |
| 6,450,950 B2 | 9/2002 | Irion | |
| 6,461,304 B1 | 10/2002 | Tanaka | |
| 6,464,631 B1 | 10/2002 | Girke | |
| 6,464,633 B1 | 10/2002 | Hosoda | |
| 6,468,201 B1 | 10/2002 | Burdick | |
| 6,468,202 B1 | 10/2002 | Irion | |
| 6,471,636 B1 | 10/2002 | Sano | |
| 6,471,637 B1 | 10/2002 | Green | |
| 6,473,116 B1 | 10/2002 | Takahashi | |
| 6,476,851 B1 * | 11/2002 | Nakamura | A61B 1/00096 |
| | | | 348/340 |
| 6,500,115 B2 | 12/2002 | Krattiger | |
| 6,514,210 B2 | 2/2003 | Ohara | |
| 6,520,908 B1 | 2/2003 | Ikeda | |
| 6,527,704 B1 | 3/2003 | Chang | |
| 6,530,881 B1 | 3/2003 | Ailinger | |
| 6,533,722 B2 | 3/2003 | Nakashima | |
| 6,545,703 B1 | 4/2003 | Takahashi | |
| 6,551,239 B2 | 4/2003 | Renner | |
| 6,554,767 B2 | 4/2003 | Tanaka | |
| 6,567,114 B2 | 5/2003 | Takahashi | |
| 6,569,084 B1 | 5/2003 | Mizuno | |
| 6,582,361 B2 | 6/2003 | Hirano | |
| 6,589,168 B2 | 7/2003 | Thompson | |
| 6,606,113 B2 | 8/2003 | Nakamura | |
| 6,618,205 B2 | 9/2003 | Murayama | |
| D481,125 S | 10/2003 | Hayamizu | |
| 6,638,212 B1 | 10/2003 | Oshima | |
| 6,638,214 B2 | 10/2003 | Akiba | |
| 6,641,531 B2 | 11/2003 | Kehr | |
| 6,656,111 B2 | 12/2003 | Fujii | |
| 6,671,099 B2 | 12/2003 | Nagata | |
| 6,677,983 B1 | 1/2004 | Takahashi | |
| 6,677,984 B2 | 1/2004 | Kobayashi | |
| 6,677,992 B1 | 1/2004 | Matsumoto | |
| 6,692,430 B2 | 2/2004 | Adler | |
| 6,692,431 B2 | 2/2004 | Kazakevich | |
| 6,699,181 B2 | 3/2004 | Wako | |
| 6,699,185 B2 | 3/2004 | Gminder | |
| 6,704,052 B1 | 3/2004 | Togino | |
| 6,712,760 B2 | 3/2004 | Sano | |
| D490,898 S | 6/2004 | Hayamizu | |
| 6,764,439 B2 | 7/2004 | Schaaf | |
| 6,778,208 B2 | 8/2004 | Takeshige | |
| 6,788,343 B1 | 9/2004 | Togino | |
| 6,793,621 B2 | 9/2004 | Butler | |
| 6,801,325 B2 | 10/2004 | Farr | |
| 6,809,499 B2 | 10/2004 | Solingen | |
| 6,809,866 B2 | 10/2004 | Xie | |
| 6,829,003 B2 | 12/2004 | Takami | |
| 6,832,984 B2 | 12/2004 | Stelzer | |
| 6,844,985 B2 | 1/2005 | Murayama | |
| 6,846,311 B2 | 1/2005 | Gatto | |
| 6,849,043 B2 | 2/2005 | Kondo | |
| 6,860,516 B2 | 3/2005 | Ouchi | |
| 6,876,380 B2 | 4/2005 | Abe | |
| 6,887,194 B2 | 5/2005 | Hart | |
| 6,888,119 B2 | 5/2005 | Iizuka | |
| 6,898,086 B2 | 5/2005 | Takami | |
| 6,899,673 B2 | 5/2005 | Ogura | |
| 6,900,829 B1 | 5/2005 | Ozawa | |
| 6,900,950 B2 | 5/2005 | Nagata | |
| 6,902,529 B2 | 6/2005 | Onishi | |
| 6,903,761 B1 | 6/2005 | Abe | |
| 6,918,693 B2 | 7/2005 | Ota | |

(56) References Cited

U.S. PATENT DOCUMENTS

| | | |
|---|---|---|
| 6,921,362 B2 | 7/2005 | Ouchi |
| 6,930,705 B2 | 8/2005 | Tanaka |
| 6,933,962 B2 | 8/2005 | Yamamoto |
| 6,937,267 B1 | 8/2005 | Takahashi |
| 6,937,269 B2 | 8/2005 | Sugimoto |
| 6,943,821 B2 | 9/2005 | Abe |
| 6,943,822 B2 | 9/2005 | Iida |
| 6,944,031 B2 | 9/2005 | Takami |
| 6,945,929 B2 | 9/2005 | Ando |
| 6,947,070 B2 | 9/2005 | Takami |
| 6,950,691 B2 | 9/2005 | Uchikubo |
| 6,956,703 B2 | 10/2005 | Saito |
| 6,967,673 B2 | 11/2005 | Ozawa |
| 6,977,670 B2 | 12/2005 | Takahashi |
| 6,980,227 B2 | 12/2005 | Iida |
| 6,982,740 B2 | 1/2006 | Adair |
| 6,985,170 B1 | 1/2006 | Tsuyuki |
| 6,992,694 B2 | 1/2006 | Abe |
| 6,995,786 B2 | 2/2006 | Abe |
| 6,997,871 B2 | 2/2006 | Sonnenschein |
| 7,027,231 B2 | 4/2006 | Miyano |
| 7,030,904 B2 | 4/2006 | Adair |
| 7,037,258 B2 | 5/2006 | Chatenever |
| 7,042,488 B2 | 5/2006 | Higuchi |
| 7,043,153 B2 | 5/2006 | Takeyama |
| 7,046,270 B2 | 5/2006 | Murata |
| 7,050,086 B2 | 5/2006 | Ozawa |
| 7,074,181 B2 | 7/2006 | Futatsugi |
| 7,074,182 B2 | 7/2006 | Rovegno |
| 7,085,064 B2 | 8/2006 | Uzawa |
| 7,097,615 B2 | 8/2006 | Banik |
| 7,104,951 B2 | 9/2006 | Hasegawa |
| 7,108,656 B2 | 9/2006 | Fujikawa |
| 7,108,657 B2 | 9/2006 | Irion et al. |
| 7,119,830 B2 | 10/2006 | Saito |
| 7,123,288 B2 | 10/2006 | Abe |
| 7,128,709 B2 | 10/2006 | Saruya |
| 7,129,472 B1 | 10/2006 | Okawa |
| 7,133,063 B2 | 11/2006 | Abe |
| D534,656 S | 1/2007 | Pilvisto |
| 7,156,863 B2 | 1/2007 | Sonnenschein |
| 7,158,314 B2 | 1/2007 | Fujii |
| 7,179,221 B2 | 2/2007 | Tsujita |
| 7,180,686 B2 | 2/2007 | Kato |
| 7,218,454 B2 | 5/2007 | Miyano |
| 7,223,231 B2 | 5/2007 | Akiba |
| 7,231,135 B2 | 6/2007 | Esenyan |
| 7,232,409 B2 | 6/2007 | Hale |
| 7,233,820 B2 | 6/2007 | Gilboa |
| 7,242,833 B2 | 7/2007 | Yang |
| 7,248,281 B2 | 7/2007 | Abe |
| 7,248,296 B2 | 7/2007 | Iketani |
| 7,252,633 B2 | 8/2007 | Obata |
| 7,255,676 B2 | 8/2007 | Higuchi |
| 7,262,797 B2 | 8/2007 | Weldum |
| 7,267,647 B2 | 9/2007 | Okada |
| 7,273,452 B2 | 9/2007 | Barbato |
| 7,277,120 B2 | 10/2007 | Gere |
| 7,280,140 B2 | 10/2007 | Henderson |
| 7,280,283 B1 | 10/2007 | Kasai |
| 7,282,025 B2 | 10/2007 | Abe |
| 7,306,588 B2 | 12/2007 | Loeb |
| 7,330,749 B1 | 2/2008 | Bhunachet |
| D564,659 S | 3/2008 | Hayashi |
| D564,660 S | 3/2008 | Hayashi |
| 7,351,202 B2 | 4/2008 | Long |
| 7,355,625 B1 | 4/2008 | Mochida |
| 7,358,987 B2 | 4/2008 | Takeshige |
| 7,365,768 B1 | 4/2008 | Ono |
| 7,371,211 B2 | 5/2008 | Akiba |
| 7,379,252 B2 | 5/2008 | Murayama |
| 7,384,308 B2 | 6/2008 | Boehnlein |
| 7,399,304 B2 | 7/2008 | Gambale |
| 7,400,341 B2 | 7/2008 | Abe |
| 7,401,984 B2 | 7/2008 | Pattie |
| 7,409,130 B2 | 8/2008 | Hatori |
| 7,420,586 B2 | 9/2008 | Higuchi |
| 7,427,263 B2 | 9/2008 | Hoeg |
| 7,431,619 B2 | 10/2008 | Boehnlein |
| 7,435,217 B2 | 10/2008 | Wiklof |
| 7,435,218 B2 | 10/2008 | Krattiger |
| 7,440,005 B2 | 10/2008 | Enomoto |
| 7,443,488 B2 | 10/2008 | Ogawa |
| 7,450,151 B2 | 11/2008 | Kaneko |
| 7,466,490 B2 | 12/2008 | Igarashi |
| 7,471,310 B2 | 12/2008 | Amling |
| 7,484,709 B2 | 2/2009 | Efinger |
| 7,486,449 B2 | 2/2009 | Miyano |
| 7,492,388 B2 | 2/2009 | Odlivak |
| 7,514,667 B2 | 4/2009 | Matsumoto |
| 7,518,632 B2 | 4/2009 | Konomura |
| 7,530,948 B2 | 5/2009 | Seibel |
| 7,542,069 B2 | 6/2009 | Tashiro |
| 7,553,276 B2 | 6/2009 | Iddan |
| 7,559,889 B2 | 7/2009 | Takahashi |
| 7,559,892 B2 | 7/2009 | Adler |
| 7,561,351 B2 | 7/2009 | Konno |
| 7,569,012 B2 | 8/2009 | Tanaka |
| 7,573,499 B2 | 8/2009 | Doguchi |
| 7,576,310 B2 | 8/2009 | Konno |
| 7,581,988 B2 | 9/2009 | Boehnlein |
| 7,582,055 B2 | 9/2009 | Komiya |
| 7,582,056 B2 | 9/2009 | Noguchi |
| 7,584,534 B2 | 9/2009 | Pease |
| 7,585,274 B2 | 9/2009 | Homma |
| 7,588,535 B2 | 9/2009 | Adler |
| 7,593,051 B2 | 9/2009 | Suda |
| 7,621,868 B2 | 11/2009 | Breidenthal |
| 7,621,869 B2 | 11/2009 | Ratnakar |
| 7,623,150 B2 | 11/2009 | Kobayashi |
| 7,627,189 B2 | 12/2009 | Donomae |
| 7,630,148 B1 * | 12/2009 | Yang .................. A61B 1/00096 359/664 |
| 7,671,888 B2 | 3/2010 | Nogami |
| 7,683,927 B2 | 3/2010 | Higuchi |
| 7,695,429 B2 | 4/2010 | Hino |
| 7,699,772 B2 | 4/2010 | Pauker |
| 7,701,650 B2 * | 4/2010 | Lin .......... A61B 1/04 359/793 |
| 7,725,013 B2 | 5/2010 | Sugimoto |
| 7,728,867 B2 | 6/2010 | Fukuyama |
| 7,734,160 B2 | 6/2010 | Sudo |
| 7,738,180 B2 * | 6/2010 | Igarashi ............. G02B 23/243 359/656 |
| 7,746,566 B2 | 6/2010 | Mizusawa |
| 7,746,572 B2 * | 6/2010 | Asami ...................... G02B 9/34 359/783 |
| 7,749,156 B2 | 7/2010 | Ouchi |
| 7,749,159 B2 | 7/2010 | Crowley |
| 7,758,495 B2 | 7/2010 | Pease |
| 7,758,499 B2 | 7/2010 | Adler |
| 7,772,786 B2 | 8/2010 | Hosoda |
| 7,773,110 B2 | 8/2010 | Abe |
| 7,773,122 B2 | 8/2010 | Irion |
| 7,773,318 B2 | 8/2010 | Takato |
| 7,775,971 B2 | 8/2010 | Fujimori |
| 7,775,973 B2 | 8/2010 | Okada |
| 7,789,822 B2 | 9/2010 | Suzuki |
| 7,800,656 B2 | 9/2010 | Takeuchi |
| RE41,807 E | 10/2010 | Yokoi |
| 7,821,529 B2 | 10/2010 | Mochida |
| 7,837,614 B2 | 11/2010 | Segawa |
| 7,841,880 B2 | 11/2010 | Ikeda |
| 7,846,090 B2 | 12/2010 | Pilvisto |
| 7,852,513 B2 | 12/2010 | Donomae |
| 7,893,956 B2 | 2/2011 | Ayrenschmalz |
| 7,896,802 B2 | 3/2011 | Otawara |
| 7,901,352 B2 | 3/2011 | Minami |
| 7,907,168 B2 | 3/2011 | Eino |
| 7,907,170 B2 | 3/2011 | Watanabe |
| 7,907,352 B2 | 3/2011 | Miyano |
| 7,914,443 B2 | 3/2011 | Uchimura |
| 7,918,788 B2 | 4/2011 | Lin |
| 7,938,773 B2 | 5/2011 | Kawai |

(56) References Cited

U.S. PATENT DOCUMENTS

| | | |
|---|---|---|
| 7,940,296 B2 | 5/2011 | Ogino |
| 7,942,814 B2 | 5/2011 | Remijan |
| 7,951,068 B2 | 5/2011 | Kura |
| 7,967,745 B2 | 6/2011 | Gilad |
| 7,976,462 B2 | 7/2011 | Wright |
| 7,995,093 B2 | 8/2011 | Takeuchi |
| 7,998,064 B2 | 8/2011 | Otawara |
| 8,002,696 B2 | 8/2011 | Suzuki |
| 8,027,101 B2 | 9/2011 | Suda |
| 8,033,992 B2 | 10/2011 | Hino |
| 8,035,684 B2 | 10/2011 | Wakito |
| 8,038,600 B2 | 10/2011 | Uchiyama |
| 8,043,207 B2 | 10/2011 | Adams |
| 8,060,172 B2 | 11/2011 | Ishihara |
| 8,063,962 B2 | 11/2011 | Hagihara |
| 8,066,631 B2 | 11/2011 | Wimmer |
| 8,072,483 B2 | 12/2011 | Tomioka |
| 8,072,537 B2 | 12/2011 | Schwarz |
| 8,072,693 B2 | 12/2011 | Togino |
| 8,075,477 B2 | 12/2011 | Nakamura |
| 8,075,478 B2 | 12/2011 | Campos |
| 8,098,441 B2 | 1/2012 | Sasamoto |
| 8,100,920 B2 | 1/2012 | Gambale |
| 8,102,415 B2 | 1/2012 | Iriyama |
| 8,105,233 B2 | 1/2012 | AbouElKheir |
| 8,113,846 B2 | 2/2012 | Wallaker |
| 8,125,514 B2 | 2/2012 | Sekiguchi |
| 8,125,515 B2 | 2/2012 | Hibi |
| 8,130,454 B2 | 3/2012 | Noguchi |
| 8,135,192 B2 | 3/2012 | Matsuzaki |
| 8,135,454 B2 | 3/2012 | Daniels |
| 8,139,296 B2 | 3/2012 | Ito |
| 8,144,191 B2 | 3/2012 | Kawanishi |
| 8,149,274 B2 | 4/2012 | Yamazaki |
| 8,152,718 B2 | 4/2012 | Cheng |
| 8,152,821 B2 | 4/2012 | Gambale |
| 8,157,798 B2 | 4/2012 | Takahashi |
| 8,164,836 B2 | 4/2012 | Uzawa |
| 8,167,791 B2 | 5/2012 | Tanaka |
| 8,167,795 B2 | 5/2012 | Hoeg |
| 8,167,796 B2 | 5/2012 | Negishi |
| 8,182,419 B2 | 5/2012 | Kohno |
| 8,187,171 B2 | 5/2012 | Irion |
| 8,187,174 B2 | 5/2012 | Wang |
| 8,189,041 B2 | 5/2012 | Konishi |
| 8,189,062 B2 | 5/2012 | Irion |
| 8,194,380 B2 | 6/2012 | Murata |
| 8,197,400 B2 | 6/2012 | Boutillette |
| 8,200,042 B2 | 6/2012 | Doi |
| 8,208,015 B2 | 6/2012 | Unsai |
| 8,211,009 B2 | 7/2012 | Tanaka |
| 8,212,862 B2 | 7/2012 | Kase |
| 8,212,863 B2 | 7/2012 | Tanaka |
| 8,221,309 B2 | 7/2012 | Iida |
| 8,221,311 B2 | 7/2012 | Campos |
| 8,223,198 B2 | 7/2012 | Shibasaki |
| 8,228,369 B2 | 7/2012 | Kojima |
| 8,229,549 B2 | 7/2012 | Whitman |
| 8,235,942 B2 | 8/2012 | Frassica |
| 8,248,414 B2 | 8/2012 | Gattani |
| 8,262,558 B2 | 9/2012 | Sato |
| 8,262,565 B2 | 9/2012 | Okada |
| 8,279,275 B2 | 10/2012 | Gono |
| 8,295,566 B2 | 10/2012 | Nishimura |
| 8,300,325 B2 * | 10/2012 | Katahira ............... G02B 9/60 359/770 |
| 8,310,529 B2 | 11/2012 | Krupnick |
| 8,334,900 B2 | 12/2012 | Qu |
| 8,345,092 B2 | 1/2013 | Takasaki |
| 8,348,835 B2 | 1/2013 | Fujimori |
| 8,360,960 B2 | 1/2013 | Sasaki |
| 8,360,964 B2 | 1/2013 | Ertas |
| 8,366,623 B2 | 2/2013 | Misono |
| 8,382,673 B2 | 2/2013 | Nagano |
| 8,394,013 B2 | 3/2013 | Ichimura |
| 8,394,014 B2 | 3/2013 | Fuerst |
| 8,425,405 B2 | 4/2013 | Mitani |
| 8,435,173 B2 | 5/2013 | Hosaka |
| 8,439,829 B2 | 5/2013 | Miyamoto |
| 8,444,547 B2 | 5/2013 | Miyamoto |
| 8,444,548 B2 | 5/2013 | Kumei |
| 8,449,456 B2 | 5/2013 | Ueno |
| 8,449,457 B2 | 5/2013 | Aizenfeld |
| 8,456,562 B2 | 6/2013 | Ishii |
| 8,460,182 B2 | 6/2013 | Ouyang |
| 8,465,421 B2 | 6/2013 | Finkman |
| 8,480,670 B2 | 7/2013 | Sugita |
| 8,491,467 B2 | 7/2013 | Miyamoto |
| 8,520,919 B2 | 8/2013 | Stepp |
| 8,523,764 B2 | 9/2013 | Hatcher |
| 8,523,766 B2 | 9/2013 | Kudoh |
| 8,764,642 B2 | 7/2014 | Bendele |
| 9,144,373 B2 | 9/2015 | Kaye |
| 10,663,714 B2 * | 5/2020 | Ofir .................. A61B 1/0011 |
| 2002/0007110 A1 | 1/2002 | Irion |
| 2002/0008732 A1 | 7/2002 | Shimizu |
| 2002/0087047 A1 | 7/2002 | Remijan |
| 2002/0109771 A1 | 8/2002 | Ledbetter |
| 2002/0109774 A1 | 8/2002 | Meron |
| 2002/0151768 A1 | 10/2002 | Akiba |
| 2002/0161281 A1 | 10/2002 | Jaffe |
| 2002/0161282 A1 | 10/2002 | Fulghum |
| 2002/0183591 A1 | 12/2002 | Matsuura |
| 2003/0030918 A1 * | 2/2003 | Murayama ............... G02B 9/34 359/691 |
| 2003/0032860 A1 | 2/2003 | Avni |
| 2003/0036681 A1 | 2/2003 | Aviv et al. |
| 2003/0055314 A1 | 3/2003 | Petitto |
| 2003/0083552 A1 * | 5/2003 | Remijan ............ G02B 23/2476 600/182 |
| 2003/0125788 A1 | 7/2003 | Long |
| 2003/0130564 A1 | 7/2003 | Martone |
| 2003/0139648 A1 | 7/2003 | Foley |
| 2003/0158462 A1 | 8/2003 | Takase |
| 2003/0181787 A1 | 9/2003 | Kondo |
| 2003/0139860 A1 | 10/2003 | Loeb |
| 2004/0015049 A1 | 1/2004 | Zaar |
| 2004/0019347 A1 | 1/2004 | Sakurai |
| 2004/0024290 A1 | 2/2004 | Root |
| 2004/0034311 A1 | 2/2004 | Mihalcik |
| 2004/0073120 A1 | 4/2004 | Motz |
| 2004/0104999 A1 | 6/2004 | Okada |
| 2004/0111012 A1 | 6/2004 | Whitman |
| 2004/0138532 A1 * | 7/2004 | Glukhovsky ...... A61B 1/00096 600/176 |
| 2004/0143162 A1 | 7/2004 | Krattiger |
| 2004/6133076 | 7/2004 | Kobayashi |
| 2004/0158129 A1 | 8/2004 | Okada |
| 2004/0160682 A1 * | 8/2004 | Miyano ................ G02B 23/243 359/784 |
| 2004/0176661 A1 | 9/2004 | Futatsugi |
| 2004/0190159 A1 * | 9/2004 | Hasegawa ................ G02B 7/38 359/697 |
| 2004/0210113 A1 | 10/2004 | Hasegawa |
| 2004/0220451 A1 | 11/2004 | Gravenstein |
| 2004/0227844 A1 * | 11/2004 | Sakamoto ............ H04N 5/2252 348/E5.026 |
| 2004/0242958 A1 | 12/2004 | Fujikawa |
| 2004/0242961 A1 | 12/2004 | Bughici |
| 2004/0249247 A1 | 12/2004 | Iddan |
| 2004/0254423 A1 | 12/2004 | Wendlandt |
| 2004/0260151 A1 | 12/2004 | Akiba |
| 2004/0267093 A1 | 12/2004 | Miyagl |
| 2005/0020876 A1 | 1/2005 | Shioda |
| 2005/0027164 A1 | 2/2005 | Barbato |
| 2005/0038317 A1 | 2/2005 | Ratnakar |
| 2005/0043583 A1 | 2/2005 | Killmann |
| 2005/0080342 A1 | 4/2005 | Gilreath |
| 2005/0090709 A1 | 4/2005 | Okada |
| 2005/0096501 A1 | 5/2005 | Stelzer et al. |
| 2005/0154255 A1 | 7/2005 | Jacobs |
| 2005/0154262 A1 | 7/2005 | Banik |
| 2005/0182295 A1 | 8/2005 | Soper |
| 2005/0203338 A1 | 9/2005 | Couvillon |

(56) References Cited

U.S. PATENT DOCUMENTS

| | | | |
|---|---|---|---|
| 2005/0234296 A1 | 10/2005 | Saadat | |
| 2005/0234347 A1 | 10/2005 | Yamataka | |
| 2005/0251127 A1 | 11/2005 | Brosch | |
| 2005/0256376 A1 | 11/2005 | Bar-Or | |
| 2005/0261553 A1 | 11/2005 | Swain | |
| 2005/0272975 A1 | 12/2005 | McWeeney | |
| 2005/0283048 A1* | 12/2005 | Gill | A61B 1/0638 600/121 |
| 2005/0284491 A1 | 12/2005 | Tashiro | |
| 2006/0004257 A1 | 1/2006 | Gilad | |
| 2006/0038318 A1 | 2/2006 | Nielson | |
| 2006/0047184 A1 | 3/2006 | Banik | |
| 2006/0052803 A1 | 3/2006 | Koitabashi | |
| 2006/0063976 A1 | 3/2006 | Aizenfeld | |
| 2006/0069307 A1 | 3/2006 | Boulais | |
| 2006/0069314 A1 | 3/2006 | Farr | |
| 2006/0149129 A1 | 7/2006 | Watts | |
| 2006/0173244 A1 | 8/2006 | Boulais | |
| 2006/0183971 A1 | 8/2006 | Haviv | |
| 2006/0183975 A1 | 8/2006 | Saadat | |
| 2006/0189845 A1 | 8/2006 | Maahs | |
| 2006/0211916 A1 | 9/2006 | Kasahara | |
| 2006/0217594 A1 | 9/2006 | Ferguson | |
| 2006/0221457 A1 | 10/2006 | Murayama | |
| 2006/0224040 A1 | 10/2006 | Khait | |
| 2006/0229499 A1 | 10/2006 | Eisenkolb | |
| 2006/0241347 A1 | 10/2006 | Whitehead | |
| 2006/0252994 A1 | 11/2006 | Ratnakar | |
| 2006/0264704 A1 | 11/2006 | Fujimori | |
| 2006/0293556 A1 | 12/2006 | Garner | |
| 2006/0293562 A1 | 12/2006 | Uchimura | |
| 2007/0015964 A1 | 1/2007 | Eversul | |
| 2007/0015968 A1 | 1/2007 | Shelnutt | |
| 2007/0019916 A1 | 1/2007 | Takami | |
| 2007/0020694 A1 | 1/2007 | Pickford | |
| 2007/0027360 A1* | 2/2007 | Mitsuya | G02B 23/243 600/129 |
| 2007/0030345 A1 | 2/2007 | Amling | |
| 2007/0049803 A1* | 3/2007 | Moriyama | A61B 1/042 600/176 |
| 2007/0055100 A1* | 3/2007 | Kato | G02B 23/24 600/109 |
| 2007/0073169 A1 | 3/2007 | Irion | |
| 2007/0078304 A1 | 4/2007 | Shimizu | |
| 2007/0083081 A1 | 4/2007 | Schlagenhauf | |
| 2007/0100206 A1 | 5/2007 | Lin | |
| 2007/0106119 A1 | 5/2007 | Hirata | |
| 2007/0115376 A1 | 5/2007 | Igarashi | |
| 2007/0118219 A1 | 5/2007 | Mitani | |
| 2007/0123748 A1 | 5/2007 | Meglan | |
| 2007/0142711 A1 | 6/2007 | Bayer | |
| 2007/0167673 A1 | 7/2007 | Enomoto | |
| 2007/0167681 A1* | 7/2007 | Gill | A61B 1/0607 600/112 |
| 2007/0173686 A1 | 7/2007 | Lin | |
| 2007/0173687 A1 | 7/2007 | Shima | |
| 2007/0182095 A1 | 7/2007 | Kimmel | |
| 2007/0177008 A1 | 8/2007 | Bayer | |
| 2007/0177009 A1 | 8/2007 | Bayer | |
| 2007/0185384 A1 | 8/2007 | Bayer | |
| 2007/0197875 A1 | 8/2007 | Osaka | |
| 2007/0203396 A1 | 8/2007 | McCutcheon et al. | |
| 2007/0206945 A1 | 9/2007 | Delorme | |
| 2007/0208225 A1 | 9/2007 | Czaniera | |
| 2007/0213590 A1 | 9/2007 | Squicclarini | |
| 2007/0213591 A1 | 9/2007 | Aizenfeld | |
| 2007/0225556 A1 | 9/2007 | Ortiz | |
| 2007/0225565 A1 | 9/2007 | Ogino | |
| 2007/0229656 A1 | 10/2007 | Khait | |
| 2007/0244353 A1 | 10/2007 | Larsen | |
| 2007/0244362 A1 | 10/2007 | El-Hachem | |
| 2007/0244366 A1 | 10/2007 | Murata | |
| 2007/0246506 A1 | 10/2007 | Hamazaki | |
| 2007/0249899 A1 | 10/2007 | Seifert | |
| 2007/0265498 A1 | 11/2007 | Ito | |
| 2007/0282165 A1 | 12/2007 | Hopkins | |
| 2007/0293720 A1 | 12/2007 | Bayer | |
| 2008/0009672 A1 | 1/2008 | Krattiger | |
| 2008/0021274 A1 | 1/2008 | Bayer | |
| 2008/0021281 A1 | 1/2008 | Fujimori | |
| 2008/0039689 A1 | 2/2008 | Yoshimitsu | |
| 2008/0039693 A1 | 2/2008 | Karasawa | |
| 2008/0045797 A1 | 2/2008 | Yasushi | |
| 2008/0051628 A1 | 2/2008 | Pecherer | |
| 2008/0051629 A1 | 2/2008 | Sugiyama | |
| 2008/0058593 A1 | 3/2008 | Gu et al. | |
| 2008/0058595 A1 | 3/2008 | Snoke | |
| 2008/0058598 A1 | 3/2008 | Ries | |
| 2008/0058601 A1 | 3/2008 | Fujimori | |
| 2008/0064931 A1 | 3/2008 | Schena | |
| 2008/0065127 A1 | 3/2008 | Adams | |
| 2008/0071290 A1 | 3/2008 | Larkin | |
| 2008/0100699 A1 | 5/2008 | Hibi | |
| 2008/0130108 A1 | 6/2008 | Bayer | |
| 2008/0139881 A1 | 6/2008 | Cover | |
| 2008/0163652 A1 | 7/2008 | Shatskin | |
| 2008/0167529 A1 | 7/2008 | Otawara | |
| 2008/0171910 A1 | 7/2008 | Kanazawa | |
| 2008/0177139 A1* | 7/2008 | Courtney | A61B 5/0035 600/109 |
| 2008/0177140 A1 | 7/2008 | Cline | |
| 2008/0188715 A1 | 8/2008 | Fujimoto | |
| 2008/0221388 A1* | 9/2008 | Seibel | A61B 1/00177 600/109 |
| 2008/0225134 A1 | 9/2008 | Amling | |
| 2008/0255425 A1 | 10/2008 | Voegele | |
| 2008/0262302 A1 | 10/2008 | Azarbarzin | |
| 2008/0262312 A1 | 10/2008 | Carroll | |
| 2008/0312497 A1 | 12/2008 | Elmouelhi | |
| 2009/0005643 A1 | 1/2009 | Smith | |
| 2009/0052061 A1 | 2/2009 | Asami | |
| 2009/0054790 A1 | 2/2009 | Czaniera | |
| 2009/0062615 A1* | 3/2009 | Yamaya | G02B 23/243 600/167 |
| 2009/0086017 A1* | 4/2009 | Miyano | G02B 23/243 348/65 |
| 2009/0093679 A1 | 4/2009 | Suigetsu | |
| 2009/0118577 A9 | 5/2009 | Snay | |
| 2009/0137869 A1 | 5/2009 | Soutorine | |
| 2009/0147076 A1 | 6/2009 | Ertas | |
| 2009/0161234 A1 | 6/2009 | Sasamoto | |
| 2009/0163769 A1 | 6/2009 | Robertson | |
| 2009/0209811 A1 | 8/2009 | Higuchi | |
| 2009/0216084 A1 | 8/2009 | Yamane | |
| 2009/0231419 A1 | 9/2009 | Bayer | |
| 2009/0237807 A1 | 9/2009 | Sasamoto | |
| 2009/0247831 A1 | 10/2009 | Miyamoto | |
| 2009/0253966 A1 | 10/2009 | Ichimura | |
| 2009/0259097 A1 | 10/2009 | Thompson | |
| 2009/0259102 A1 | 10/2009 | Koninckx | |
| 2009/0268011 A1 | 10/2009 | Scott | |
| 2009/0284649 A1 | 11/2009 | Pease | |
| 2009/0287047 A1 | 11/2009 | Onoda | |
| 2009/0287192 A1 | 11/2009 | Vivenzio | |
| 2009/0290236 A1 | 11/2009 | Wang | |
| 2009/0299137 A1* | 12/2009 | Gal | A61B 1/0623 600/109 |
| 2009/0299144 A1 | 12/2009 | Shigemori | |
| 2009/0306474 A1 | 12/2009 | Wilson | |
| 2009/0306476 A1 | 12/2009 | Banik | |
| 2009/0318757 A1 | 12/2009 | Singh | |
| 2010/0010301 A1 | 1/2010 | Hale | |
| 2010/0010302 A1 | 1/2010 | Hadani | |
| 2010/0013914 A1 | 1/2010 | Bettesh | |
| 2010/0016673 A1 | 1/2010 | Bandy | |
| 2010/0030020 A1 | 2/2010 | Sanders | |
| 2010/0042097 A1 | 2/2010 | Newton | |
| 2010/0047733 A1 | 2/2010 | Nahlieli | |
| 2010/0053312 A1 | 3/2010 | Watanabe | |
| 2010/0073470 A1 | 3/2010 | Takasaki | |
| 2010/0076268 A1* | 3/2010 | Takasugi | A61B 1/05 600/171 |
| 2010/0081874 A1 | 4/2010 | Miyamoto | |

(56) References Cited

U.S. PATENT DOCUMENTS

| | | |
|---|---|---|
| 2010/0081875 A1 | 4/2010 | Fowler |
| 2010/0087706 A1 | 4/2010 | Syed |
| 2010/0121142 A1 | 5/2010 | Ouyang |
| 2010/0123950 A1* | 5/2010 | Fujiwara ............... G02B 21/02 359/368 |
| 2010/0130822 A1 | 5/2010 | Katayama |
| 2010/0137682 A1 | 6/2010 | Doguchi |
| 2010/0137687 A1 | 6/2010 | Schwartz |
| 2010/0141746 A1 | 6/2010 | Ikeda |
| 2010/0152612 A1 | 6/2010 | Headley |
| 2010/0160729 A1 | 6/2010 | Smith |
| 2010/0174144 A1 | 7/2010 | Hsu |
| 2010/0185056 A1 | 7/2010 | Gordon |
| 2010/0187408 A1 | 7/2010 | Klem |
| 2010/0201985 A1 | 8/2010 | Wang |
| 2010/0204609 A1 | 8/2010 | Worth |
| 2010/0217076 A1 | 8/2010 | Ratnakar |
| 2010/0217081 A1 | 8/2010 | Deppmeier |
| 2010/0228086 A1 | 9/2010 | Ohki |
| 2010/0245653 A1* | 9/2010 | Bodor ............... H04N 5/2254 348/335 |
| 2010/0249496 A1 | 9/2010 | Cardenas |
| 2010/0249513 A1 | 9/2010 | Tydlaska |
| 2010/0256447 A1 | 10/2010 | Dubi |
| 2010/0286475 A1 | 11/2010 | Robertson |
| 2010/0296178 A1* | 11/2010 | Genet ............... G02B 27/0025 359/754 |
| 2010/0298640 A1 | 11/2010 | Oneda |
| 2010/0298773 A1 | 11/2010 | Nitsan |
| 2010/0305503 A1 | 12/2010 | Fang |
| 2010/0317919 A1 | 12/2010 | Takaoka |
| 2010/0317921 A1 | 12/2010 | Marple |
| 2010/0318061 A1 | 12/2010 | Derrick |
| 2010/0326703 A1 | 12/2010 | Gilad |
| 2011/0028790 A1 | 2/2011 | Farr |
| 2011/0054256 A1 | 3/2011 | Cushner |
| 2011/0112363 A1 | 5/2011 | Koga |
| 2011/0157596 A1* | 6/2011 | Wax ............... A61B 5/0084 356/456 |
| 2011/0160530 A1 | 6/2011 | Ratnakar |
| 2011/0169931 A1* | 7/2011 | Pascal ............... A61B 1/041 348/68 |
| 2011/0184243 A1 | 7/2011 | Wright |
| 2011/0196200 A1 | 8/2011 | Glozman |
| 2011/0196204 A1 | 8/2011 | Setty |
| 2011/0211267 A1* | 9/2011 | Takato ............... G02B 13/04 359/784 |
| 2011/0224487 A1 | 9/2011 | Ogawa |
| 2011/0245600 A1 | 10/2011 | Ishii |
| 2011/0245609 A1 | 10/2011 | Laser |
| 2011/0257478 A1 | 10/2011 | Kleiner |
| 2011/0263938 A1 | 10/2011 | Levy |
| 2011/0282144 A1 | 11/2011 | Gettman |
| 2011/0282148 A1 | 11/2011 | Kase |
| 2011/0288374 A1 | 11/2011 | Hadani |
| 2011/0295061 A1 | 12/2011 | Haramaty |
| 2011/0295062 A1 | 12/2011 | GratacosSolsona |
| 2011/0295064 A1 | 12/2011 | Kagawa |
| 2011/0306832 A1 | 12/2011 | Bassan |
| 2011/0313249 A1 | 12/2011 | Viola |
| 2012/0010465 A1 | 1/2012 | Erikawa |
| 2012/0029291 A1 | 2/2012 | Wallace |
| 2012/0040305 A1 | 2/2012 | Karazivan |
| 2012/0041534 A1 | 2/2012 | Clerc |
| 2012/0046524 A1 | 2/2012 | Miyamoto |
| 2012/0053407 A1 | 3/2012 | Levy |
| 2012/0057251 A1* | 3/2012 | Takato ............... G02B 23/243 359/749 |
| 2012/0065468 A1 | 3/2012 | Levy |
| 2012/0071748 A1 | 3/2012 | Mark |
| 2012/0078042 A1 | 3/2012 | Uram |
| 2012/0088965 A1 | 4/2012 | Stokes |
| 2012/0095391 A1 | 4/2012 | Bendele |
| 2012/0104230 A1 | 5/2012 | Eismann |
| 2012/0147254 A1* | 6/2012 | Adachi ............... G02B 13/18 348/345 |
| 2012/0178995 A1 | 7/2012 | Newton |
| 2012/0209062 A1 | 8/2012 | Qiao |
| 2012/0229615 A1* | 9/2012 | Kirma ............... A61B 1/0638 348/68 |
| 2012/0232340 A1 | 9/2012 | Levy |
| 2012/0232342 A1 | 9/2012 | Reydel |
| 2012/0232343 A1 | 9/2012 | Levy |
| 2012/0253121 A1 | 10/2012 | Kitano |
| 2012/0253284 A1 | 10/2012 | Nitsan |
| 2012/0259175 A1 | 10/2012 | Reydel |
| 2012/0265094 A1 | 10/2012 | Goldfarb |
| 2013/0012778 A1 | 1/2013 | Bayer |
| 2013/0012794 A1 | 1/2013 | Zeng |
| 2013/0060086 A1 | 3/2013 | Talbert |
| 2013/0109916 A1 | 5/2013 | Levy |
| 2013/0109918 A1 | 5/2013 | Pagan |
| 2013/0110003 A1 | 5/2013 | Surti |
| 2013/0131445 A1 | 5/2013 | Zerfas |
| 2013/0131447 A1 | 5/2013 | Benning |
| 2013/0131454 A1 | 5/2013 | McCormack |
| 2013/0137930 A1* | 5/2013 | Menabde ............... G02B 23/243 600/168 |
| 2013/0172670 A1 | 7/2013 | Levy |
| 2013/0172673 A1 | 7/2013 | Kennedy |
| 2013/0172674 A1 | 7/2013 | Kennedy |
| 2013/0172677 A1 | 7/2013 | Kennedy |
| 2013/0172678 A1 | 7/2013 | Kennedy |
| 2013/0190561 A1 | 7/2013 | Oskin |
| 2013/0194404 A1 | 8/2013 | Christiansen |
| 2013/0204088 A1 | 8/2013 | Miyamoto |
| 2013/0217965 A1* | 8/2013 | Sasamoto ............... A61B 1/018 600/109 |
| 2013/0253272 A1 | 9/2013 | Takahashi |
| 2013/0267778 A1 | 10/2013 | Rehe |
| 2013/0296649 A1* | 11/2013 | Kirma ............... G02B 13/005 600/109 |
| 2013/0314521 A1 | 11/2013 | Satake |
| 2013/0317295 A1 | 11/2013 | Morse |
| 2014/0296866 A1* | 10/2014 | Salman ............... A61B 1/015 606/109 |
| 2014/0364691 A1* | 12/2014 | Krivopisk ............... A61B 1/05 600/109 |

FOREIGN PATENT DOCUMENTS

| | | |
|---|---|---|
| CN | 1988841 | 6/2007 |
| CN | 2936129 Y | 8/2007 |
| CN | 101061940 A | 10/2007 |
| CN | 201108422 Y | 9/2008 |
| CN | 101385633 A | 3/2009 |
| CN | 101396258 | 4/2009 |
| CN | 101926171 | 12/2010 |
| CN | 102058375 A | 5/2011 |
| CN | 102058380 A | 5/2011 |
| CN | 101061940 | 6/2011 |
| CN | 201870615 U | 6/2011 |
| CN | 102469924 | 5/2012 |
| DE | 102005008153 A1 | 11/2005 |
| EP | 0029555 A2 | 6/1981 |
| EP | 543738 A1 | 5/1993 |
| EP | 0710039 A2 | 5/1996 |
| EP | 730844 | 9/1996 |
| EP | 1195630 A2 | 4/2002 |
| EP | 1325458 | 7/2003 |
| EP | 1347702 A2 | 10/2003 |
| EP | 948283 B1 | 4/2004 |
| EP | 1073365 B1 | 7/2005 |
| EP | 1627595 A1 | 2/2006 |
| EP | 668738 B1 | 6/2006 |
| EP | 1535565 | 6/2006 |
| EP | 1685790 A1 | 8/2006 |
| EP | 1472972 B1 | 10/2006 |
| EP | 1790280 A1 | 5/2007 |
| EP | 1834572 A1 | 9/2007 |
| EP | 1952750 | 8/2008 |
| EP | 1977675 | 10/2008 |

(56) References Cited

FOREIGN PATENT DOCUMENTS

| | | |
|---|---|---|
| EP | 1977682 A2 | 10/2008 |
| EP | 1974000653 | 10/2008 |
| EP | 1992292 A1 | 11/2008 |
| EP | 2022389 A1 | 2/2009 |
| EP | 2144571 A2 | 1/2010 |
| EP | 2276389 A1 | 1/2011 |
| EP | 1835847 B1 | 5/2011 |
| EP | 1870014 B1 | 1/2012 |
| EP | 2501271 A1 | 9/2012 |
| EP | 2503933 A1 | 10/2012 |
| EP | 2512577 A2 | 10/2012 |
| EP | 2529660 A1 | 12/2012 |
| EP | 2596756 A1 | 5/2013 |
| EP | 2623019 A1 | 8/2013 |
| GB | 2321132 | 7/1998 |
| GB | 2352922 A | 2/2001 |
| JP | S5551270 | 5/1980 |
| JP | 55078932 | 6/1980 |
| JP | 61055657 | 11/1986 |
| JP | S6296616 | 6/1987 |
| JP | H0253701 | 4/1990 |
| JP | H02188709 A | 7/1990 |
| JP | H02188709 A | 7/1990 |
| JP | H03116801 | 12/1991 |
| JP | H04341232 | 11/1992 |
| JP | 5049000594 | 3/1993 |
| JP | H05309069 | 11/1993 |
| JP | 6105000800 | 4/1994 |
| JP | 7000000352 | 1/1995 |
| JP | 8122000557 | 5/1996 |
| JP | 1013007179 | 4/1998 |
| JP | 1015001113 | 6/1998 |
| JP | 11125773 | 5/1999 |
| JP | 11137512 | 5/1999 |
| JP | H11125773 | 5/1999 |
| JP | H11125773 A | 5/1999 |
| JP | 1116009340 | 6/1999 |
| JP | 1116009341 | 6/1999 |
| JP | H11253401 | 9/1999 |
| JP | 2000171727 A | 6/2000 |
| JP | 2000325386 | 11/2000 |
| JP | 2000330015 A | 11/2000 |
| JP | 2001061762 | 3/2001 |
| JP | 2001198086 | 7/2001 |
| JP | 2002000559 | 1/2002 |
| JP | 2002017667 | 1/2002 |
| JP | 2002058636 | 2/2002 |
| JP | 200265589 A | 3/2002 |
| JP | 2002065575 | 3/2002 |
| JP | 2002078675 | 3/2002 |
| JP | 2002216902 | 8/2002 |
| JP | 2002291693 | 10/2002 |
| JP | 2003038431 | 2/2003 |
| JP | 2003081900 | 3/2003 |
| JP | 2003111724 | 4/2003 |
| JP | 2003190082 | 7/2003 |
| JP | 2003220017 | 8/2003 |
| JP | 2003245247 | 9/2003 |
| JP | 2004022391 | 1/2004 |
| JP | 2004049754 | 2/2004 |
| JP | 2004049756 | 2/2004 |
| JP | 2004199834 | 4/2004 |
| JP | 2004205779 A | 7/2004 |
| JP | 2004354888 A | 12/2004 |
| JP | 2005013557 A | 1/2005 |
| JP | 2005058547 | 3/2005 |
| JP | 2095253543 | 9/2005 |
| JP | 2005323874 A | 11/2005 |
| JP | 2006003549 A | 1/2006 |
| JP | 3765500 | 2/2006 |
| JP | 2006068109 | 3/2006 |
| JP | 2006068109 A | 3/2006 |
| JP | 2006218155 | 8/2006 |
| JP | 2006280954 | 10/2006 |
| JP | 2086288758 | 10/2006 |
| JP | 2007020866 A | 2/2007 |
| JP | 2007185276 | 7/2007 |
| JP | 2008068025 | 3/2008 |
| JP | 2008118568 | 5/2008 |
| JP | 2008161569 A | 7/2008 |
| JP | 2008229204 | 10/2008 |
| JP | 2008257108 A | 10/2008 |
| JP | 2009233186 | 10/2009 |
| JP | 2009251574 | 10/2009 |
| JP | 4445647 | 4/2010 |
| JP | 2010178766 A | 8/2010 |
| JP | 2010279539 | 12/2010 |
| WO | 9219148 A1 | 11/1992 |
| WO | 00052643 A1 | 9/2000 |
| WO | 2002045595 | 6/2002 |
| WO | 2004026125 | 4/2004 |
| WO | WO 2004/112594 A1 | 12/2004 |
| WO | 2005082228 A1 | 9/2005 |
| WO | 2006073581 | 7/2006 |
| WO | 2006105932 A1 | 10/2006 |
| WO | 2007113801 A2 | 10/2007 |
| WO | 2007087421 | 11/2007 |
| WO | 2007136859 A2 | 11/2007 |
| WO | 2008012813 A1 | 1/2008 |
| WO | 2008073243 | 6/2008 |
| WO | 2008093288 | 8/2008 |
| WO | 2008139770 | 11/2008 |
| WO | 2008155776 | 12/2008 |
| WO | 2008156623 | 12/2008 |
| WO | 2009009414 | 1/2009 |
| WO | 2009025343 | 2/2009 |
| WO | 2009040744 | 4/2009 |
| WO | 2909095915 | 8/2009 |
| WO | 2010021342 | 2/2010 |
| WO | 2010028612 | 3/2010 |
| WO | 2010045406 | 4/2010 |
| WO | 2010066788 | 6/2010 |
| WO | 2010084506 | 6/2010 |
| WO | 2010146587 | 12/2010 |
| WO | 2010146587 A1 | 12/2010 |
| WO | 2011008922 | 1/2011 |
| WO | 2011041724 | 4/2011 |
| WO | 2011083451 | 7/2011 |
| WO | 2011126812 | 10/2011 |
| WO | 2012038958 | 3/2012 |
| WO | 2013131578 | 3/2012 |
| WO | 2012056453 | 5/2012 |
| WO | 2012077116 | 6/2012 |
| WO | 2012077117 | 6/2012 |
| WO | 2012088201 A2 | 6/2012 |
| WO | 2012103266 | 8/2012 |
| WO | 2012128507 | 9/2012 |
| WO | 2012153324 | 11/2012 |
| WO | 2013014673 | 1/2013 |
| WO | 2013024476 | 2/2013 |
| WO | 2013043704 | 3/2013 |
| WO | 2013128136 | 9/2013 |
| WO | 2013144944 | 10/2013 |
| WO | 2014061023 | 4/2014 |

OTHER PUBLICATIONS

Extended European Search Report for application No. EP12755186, completed on May 23, 2016.
Second Office Action for Chinese Patent Application No. 201180067259.2, dated Mar. 30, 2016.
Supplementary European Search Report for EP13847670, completed on May 19, 2016.
Offce Action dated Apr. 28, 2016 for U.S. Appl. No. 13/992,014.
Notice of Allowance dated Aug. 26, 2016 for U.S. Appl. No. 13/212,627.
Office Action dated Sep. 18, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Notice of Allowance dated Nov. 9, 2016 for U.S. Appl. No. 13/557,114.

(56) References Cited

OTHER PUBLICATIONS

Third Office Action for Chinese Patent Application No. 201180067259.2, dated Oct. 21, 2016.
Office Action for Chinese Patent Application No. 201180062736.6, dated Dec. 23, 2016.
Office Action for Japanese Patent Application No. 2016-105009, dated Jan. 16, 2017.
Office Action for Chinese Patent Application No. 201380053351.2, dated Dec. 13, 2016.
First Office Action for EP11847191.1, dated Feb. 21, 2017.
Office Action dated Mar. 21, 2017 for U.S. Appl. No. 13/992,014.
Nofice of Allowance dated Apr. 18, 2017 for U.S. Appl. No. 13/713,449.
Examination Report for EP11846069.0, dated Feb. 21, 2017.
Extended European Search Report for EP11826512.3, dated Apr. 6, 2017.
Office Action dated May 23, 2017 for U.S. Appl. No. 13/655,120.
Brochure for US Endoscopy's AquaShield Water Bottle System, 2010.
First Image of an Endo Smart Cap, made by Medivators, and obtained from http://www.bymemedical.com/prod/145t.jpg and advertised at http://www.medivators.com/products/endoscopy-procedure-products/irrigation-tubing/endo-smartcap%C2%AE.
International Search Report for PCT/EP2009/066726, dated Aug. 16, 2010.
International Search Report for PCT/IL2011/000832, dated May 16, 2012.
International Search Report for PCT/IL2011/050049, dated May 15. 2012.
International Search Report for PCT/IL2011/050050, dated May 16, 2012.
International Search Report for PCT/IL2012/050037, dated Jun. 1, 2012.
International Search Report for PCT/IL2012/050274, dated Nov. 15, 2012.
International Search Report for PCT/IL2012/050299, dated Nov. 15, 2012.
International Search Report for PCT/IL2013/050840, dated Feb. 2, 2014.
International Search Report of PCT/IL10/00476 dated Sep. 27, 2010, 2 pages.
International Search Report of PCT/IL2011/000745, dated May 8, 2012.
Office Action dated Feb. 17, 2015 for U.S. Appl. No. 13/882,004.
First Office Action for CN 2012800171292, dated Feb. 28, 2015.
Office Action dated Mar. 12, 2015 for U.S. Appl. No. 13/822,908.
Office Action dated Feb. 13, 2015 for U.S. Appl. No. 13/713,449.
Office Action dated Mar. 6, 2015 for U.S. Appl. No. 13/413,059.
Office Action dated Nov. 26, 2014 for U.S. Appl. No. 13/713,466.
Office Action dated Jun. 3, 2015 for U.S. Appl. No. 13/992,014.
Office Action dated May 1, 2015 for U.S. Appl. No. 13/992,021.
Office Action dated Jan. 15, 2015 for U.S. Appl. No. 13/190,968.
Office Action dated Aug. 6, 2015 for U.S. Appl. No. 13/119,032.
Office Action dated Aug. 4, 2016 for U.S. Appl. No. 13/557,114.
Office Action for Chinese Patent Application No. 201180067269.2, dated May 29, 2015.
Office Action dated Aug. 19, 2015 for U.S. Appl. No. 13/713,466.
Office Action dated Aug. 18, 2015 for U.S. Appl. No. 13/713,449.
First Office Action for CN 2012800368972, dated Jun. 1, 2015.
Office Action dated Aug. 5, 2015 for U.S. Appl. No. 13/212,627.
Office Action dated Jul. 21, 2015 for U.S. Appl. No. 13/992,021.
First office action for CN2011800627366, dated Feb. 25, 2015.
Notice of Allowance dated Jun. 8, 2015 for U.S. Appl. No. 13/984,028.
Notice of Allowance dated Jun. 8, 2015 for U.S. Appl. No. 13/419,252.
Prosecution File History for U.S. Appl. No. 13/190,968, filed Jul. 26, 2011 through Jun. 17, 2015.
Notice of Allowance dated Jun. 17, 2016 for U.S. Appl. No. 13/190,068.
Supplementary European Search Report for European Application No. EP12823972, dated May 13, 2015.
Extended European Search Report for EP14196113.8, dated Apr. 1, 2015.
Corrected European Search Opinion for EP14186113.8, dated Apr. 29, 2015.
Office Action dated Oct. 7, 2015 for U.S. Appl. No. 13/882,004.
Office Action for Japanese Patent Application No. JP2014-525562, dated Apr. 26, 2016.
Office Action dated Nov. 16, 2015 for U.S. Appl. No. 13/557,114.
Office Action for Japanese Patent Application No. JP2014-522214, dated Apr. 26, 2016.
Office Action dated Aug. 27, 2015 for U.S. Appl. No. 13/655,120.
Supplementary European Search Report for EP11847191I, dated Jan. 16, 2015.
Examination Search Report for Canadian Patent Application No. CA2765559, dated Jan. 18, 2016.
Office Action for Chinese Patent Application No. 201280038808.8, dated May 20, 2015.
Second Office Action for Chinese Patent Applicatio No. CN201280038808.8, dated Feb. 25, 2016.
Examination Report for Canadian Patent Application No. CA2765559, dated Jan. 18, 2016.
Corrected European Search Opinion for EP14166113.8, dated Apr. 29, 2015.
Extended European Search Report for EP12817452.1, dated Mar. 9, 2015.
Notice of Allowance dated Dec. 15, 2014 for U.S. Appl. No. 13/713,466.
Notice of Allowance dated Dec. 15, 2015 for U.S. Appl. No. 13/713,466.
Office Action dated Jan. 12, 2016 for U.S. Appl. No. 13/713,466.
Office Action for Japanese Patent Application No. 2013-542668, dated Oct. 1, 2015.
Office Action for Japanese Patent Application No. 2013-535586, dated Sep. 24, 2015.
Second office action for Chinese Patent Application No. 201180062736.6, dated Oct. 12, 2015.
Notice of Allowance dated Dec. 23, 2015 for U.S. Appl. No. 13/992,021.
Office Action dated Dec. 4, 2015 for U.S. Appl. No. 13/822,908.
Office Action dated Nov. 24, 2015 for U.S. Appl. No. 13/413,059.
Office Action dated Nov. 3, 2015 for U.S. Appl. No. 13/992,014.
Extended European Search Report for EP11846069.0, dated Apr. 24, 2014.
First Office Action for Chinese Patent Applicatio No. CN201380063351.2, dated Mar. 2, 2016.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Second image of an Endo Smart Cap, made by Medivators, and obtained from http://oymemedical.com/prod/150L.jpg and advertised at http://www.medivators.com/products/endoscopy-procedure-products/irrigation-tubing/endo-smartcap%C2%AE.

* cited by examiner

OPTICAL SYSTEMS FOR MULTI-SENSOR ENDOSCOPES

CROSS-REFERENCE TO RELATED APPLICATIONS

This application is a continuation of U.S. patent application Ser. No. 15/092,970, entitled "Optical Systems for Multi-Sensor Endoscopes" and filed on Apr. 7, 2016, which is continuation of U.S. patent application Ser. No. 13/882,004, of the same title and filed on May 23, 2013, which is a national stage entry of PCT Application Number PCT/IL2011/000832, of the same title and filed on Oct. 27, 2011, which relies on U.S. Provisional Patent Application No. 61/407,495, of the same title and filed on Oct. 28, 2010, for priority, all of which are hereby incorporated by reference in their entirety.

FIELD OF THE INVENTION

This invention relates to a wide FOV objective lens system for an endoscope.

BACKGROUND

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various surgical tools may be inserted through a working channel in the endoscope for performing different surgical procedures.

There are known various endoscopes employing in their front insertion part, optical heads for viewing the interior of a body cavity or lumen such as the lower digestive track. Such optical head normally includes at least an illumination means for illuminating the object, an objective lens system and a sensor array.

U.S. Pat. No. 6,956,703 discloses an objective lens for endoscopes comprises a front lens unit component and a rear lens unit component, between which a aperture stop is located, wherein the front lens unit component comprises, in order from the object side, a first lens having a negative refractive power, and a second lens having a positive refractive power which directs a surface of the small radius of curvature toward the object side; wherein the rear lens unit component comprises a third lens having a positive refractive power which directs a surface of the small radius of curvature toward the image side, a fourth lens having a positive refractive power, and a fifth lens having a negative refractive power; and wherein the fourth lens and the fifth lens are cemented. The following condition is satisfied: $2.0<|f3/f|<3.0$ where f is the composite focal length of the total system and f 3 is the focal length of the third lens. Still, the complexity of the objects that are inspected by the endoscope (for example, the asymmetric colon environment), requires high quality images capturing a wide Field of View (FOV), which cannot be accomplished using only one detector.

More efforts have been undertaken to improve the optical design of these systems and to create a wide FOV, as seen for example, in U.S. Pat. No. 5,870,234 entitled "Compact wide angle lens", as well as U.S. Pat. No. 6,476,851 entitled "Electronic endoscope". Although these patents bring the advantage of a wide FOV they mainly provide a front view. Another disadvantage is a significant distortion in the periphery looking at the borders of the wide view image.

These disadvantages may be partially solved by using a multi image lens for example as shown in US patent application number 2005/0168616 entitled "Methods and apparatus for capturing images with a multi-image lens" or by using other Omni-directional optical solutions, as disclosed, for example, in U.S. Pat. No. 7,362,516 entitled "Optical lens providing Omni-directional coverage and illumination". These technologies may support a wide FOV with relatively low distortion in the periphery of the image however they suffer from a major disadvantage of low optical resolution on side views. Another disadvantage of these technologies is the complexity and space consuming design which typically eliminates the possibility to combine other crucial features like jet, working channels and illuminating sources to the endoscope.

There is still a need in the art for endoscopes, such as colonoscopies, that provide a wide FOV, a wide range of Depth of Field/Depth of Focus (DOF) and acceptable resolution within the required dimensions of the device used of a medical application.

SUMMARY

The following embodiments and aspects thereof are described and illustrated in conjunction with systems, tools and methods which are meant to be exemplary and illustrative, not limiting in scope.

It is an object of the current invention to provide optical system(s) for front looking and side looking cameras to be housed in the same head (tip) of an endoscope. The cameras together with their respective optic systems are adapted to provide a high quality image capturing a wide FOV of the complex environment examined by the use of the endoscope. According to some embodiments, there is provided an endoscope comprising at least a front looking camera and a side looking camera being essentially perpendicular to one another. According to some embodiments any of the cameras may include a small-sized image sensors such as CCD or CMOS sensors (hereinafter referred to as CCD but can also mean CMOS or any other sensor). In order to keep the outer diameter of the front part of the endoscope as small as possible, the optical systems used in the plurality of cameras need to be compact. Specifically, the optical track of the side looking camera needs to be short. In the case where two side looking cameras are positioned along the same axis, preferably essentially, perpendicular to the long axis of the endoscope, the minimal diameter of the endoscope's head is limited to at least twice the total length of the cameras (which typically includes the optical track of the camera, the sensor, and any electronic circuitry and wiring which may be located behind the sensor). Shortening the total length should not affect the FOV or cause distortion. Both optical characteristics should be maintained together with minimal total length.

Additionally, working channel(s) and fluid channel(s) need to traverse the endoscope's head. Thus, the diameter of the cameras and its optical systems needs to be small to allow for space occupied by the channels. Since different sensors may be used per field of view it opens the opportunity for additional working channels space giving big advantage to this application.

In order to effectively work within the confined space in a body cavity, the cameras may be equipped with wide-angle lens, capable of imaging close objects and a wide range of working distances with preservation of image quality.

Optionally, several optical modules (cameras) in one endoscope head, with similar or different designs may be used, optionally each tuned to its desired Depth of Field (DOF).

According to some embodiments, there is provided herein an optical system for a tip section of a multi-sensor endoscope, the system comprising: a front-pointing camera sensor; a front objective lens system; a side-pointing camera sensor; and a side objective lens system, wherein at least one of the front and side objective lens systems comprises a front sub-system and a rear sub-system separated by a stop diaphragm, wherein the front sub-system comprises, in order from the object side, a first front negative lens and a second front positive lens, the rear sub-system comprises, in order from the object side, a first rear positive lens, an achromatic sub-assembly comprising a second rear positive lens and a third rear negative lens, wherein the following condition is satisfied:

$f_{(first\ rear\ positive\ lens)} \leq 1.8f$, where f is the composite focal length of the total lens system and $f_{(first\ rear\ positive\ lens)}$ is the focal length of the first rear positive lens.

The front sub-system may further include an additional front positive lens (such as a meniscus lens) disposed between the first front negative lens and the second front positive lens (as seen, for example, in FIG. 4c).

The rear sub-system may further include a rear protective glass situated between the third rear negative lens and the front-pointing and/or side-pointing camera sensor, wherein the rear protective glass is adapted to protect a detector array of the front-pointing and/or side-pointing camera sensor.

According to some embodiments, the front-pointing camera sensor and the front objective lens system may be adapted to provide a Depth of Focus (DOF) of between 4 and 110 mm. Optical system having a Depth of Focus (DOF) of between 4 and 110 mm may mean that the optical system is adapted to image objects at an object distance of 4-110 mm. The front-pointing camera sensor and the front objective lens system may be adapted to provide a Depth of Focus (DOF) of between 3.5 and 50 mm. The front-pointing camera sensor and the front objective lens system may be adapted to provide an effective spatial resolution of at least 60 lines per mm at Depth of Focus (DOF) of between 5 and 50 mm. The front-pointing camera sensor and the front objective lens system may be adapted to provide an effective angular resolution of about 2' per degree or less at Depth of Focus (DOF) of between 5 and 50 mm. The front-pointing camera sensor and the front objective lens system may be adapted to provide a Field of View (FOV) of at least 150 degrees. The front-pointing camera sensor and the front objective lens system may be adapted to provide a Field of View (FOV) of at least 170 degrees.

According to some embodiments, the front-pointing camera sensor and the front objective lens system have a total optical length of 5 mm or less.

According to some embodiments, the side-pointing camera sensor and the side objective lens system may be adapted to provide a Depth of Focus (DOF) of between 3.5 and 50 mm. The side-pointing camera sensor and the side objective lens system may be adapted to provide an effective spatial resolution of at least 60 lines per mm at Depth of Focus (DOF) of between 5 and 50 mm. The side-pointing camera sensor and the side objective lens system may be adapted to provide a Depth of Focus (DOF) of between 3 and 30 mm. The side-pointing camera sensor and the side objective lens system may be adapted to provide an effective angular resolution of about 2' per degree or less at Depth of Focus (DOF) of between 4.5 and 25 mm. The side-pointing camera sensor and the side objective lens system may be adapted to provide a Field of View (FOV) of at least 150 degrees. The side-pointing camera sensor and the side objective lens system may be adapted to provide a Field of View (FOV) of at least 170 degrees.

According to some embodiments, the side-pointing camera sensor and the side objective lens system may have a total optical length of 5 mm or less (for example, 4 mm or less, 3 mm or less).

According to some embodiments, the diameter of the first front negative lens may be 2.5 mm or less (without the barrel or lens holder).

According to some embodiments, there is provided an objective lens system for at least one of a front-pointing camera sensor and a side-pointing camera sensor of a multi-sensor endoscope, the objective lens system comprising: a front sub-system and a rear sub-system separated by a stop diaphragm, wherein the front sub-system comprises a first front negative lens and a second front positive lens, and the rear sub-system comprises a first rear positive lens, an achromatic sub-assembly comprising a second rear positive lens and a third rear negative lens, wherein the following condition is satisfied:

$f_{(first\ rear\ positive\ lens)} \leq 1.8f$, where f is the composite focal length of the total lens system and f(first rear positive lens) is the focal length of the first rear positive lens.

According to some embodiments, there is provided a tip section of a multi-sensor endoscope comprising an optical system comprising: a front-pointing camera sensor; a front objective lens system; a side-pointing camera sensor; and a side objective lens system, wherein at least one of the front and side objective lens systems comprises a front sub-system and a rear sub-system separated by a stop diaphragm, the front sub-system comprises a first front negative lens and a second front positive lens, the rear sub-system comprises a first rear positive lens, an achromatic sub-assembly comprising a second rear positive lens and a third rear negative lens, wherein the following conditions are satisfied:

$f_{(first\ rear\ positive\ lens)} \leq 1.8f$, where f is the composite focal length of the total lens system and $f_{(first\ rear\ positive\ lens)}$ is the focal length of the first rear positive lens.

More details and features of the current invention and its embodiments may be found in the description and the attached drawings.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In order to understand the invention and to see how it may be carried out in practice, embodiments will now be described, by way of non-limiting example only, with reference to the accompanying drawings, in which.

DETAILED DESCRIPTION

Figure 1A:
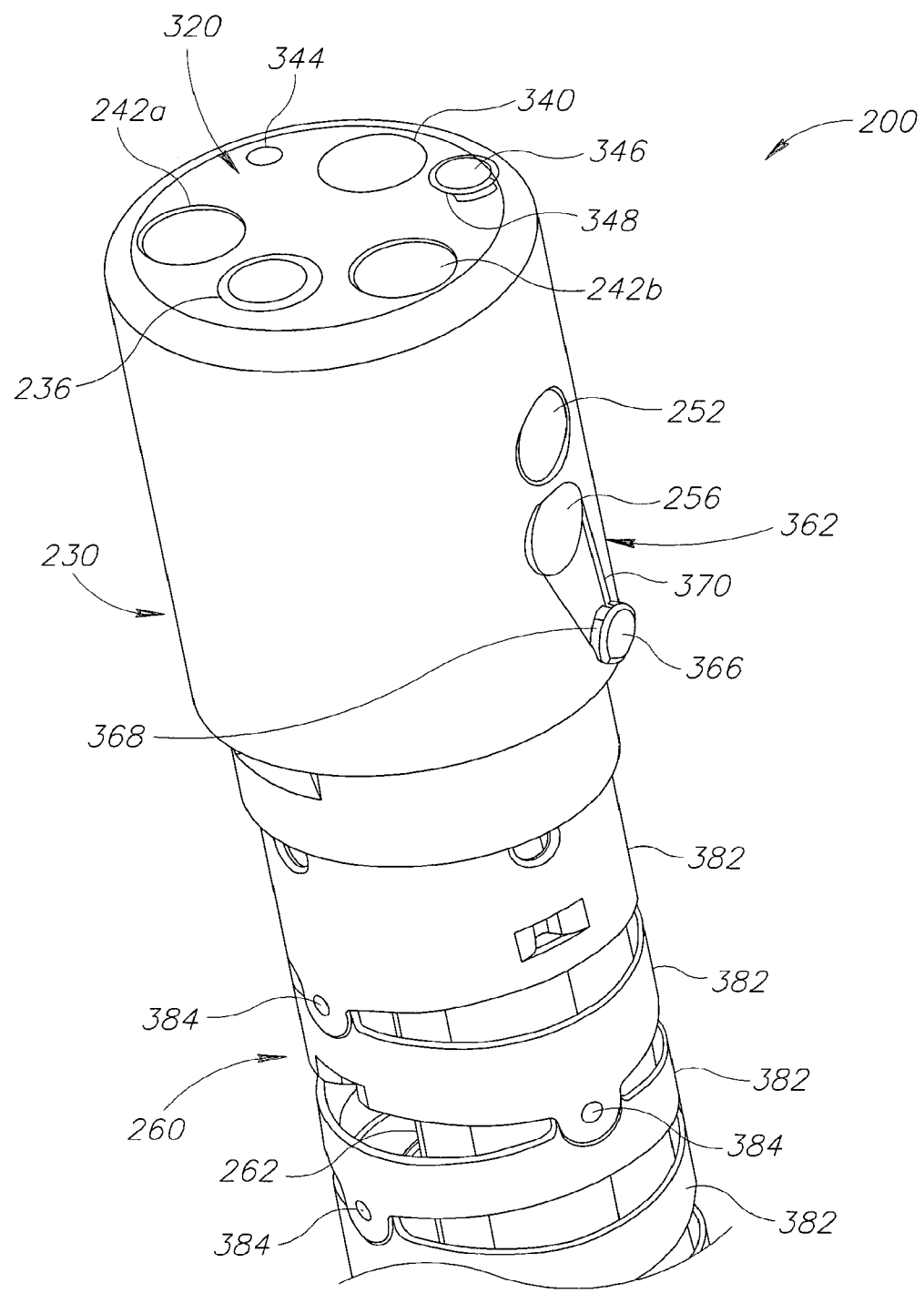
FIG. 1a schematically depicts an external isometric view of an endoscope having multiple fields of view according to an exemplary embodiment of the current invention.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The terms "comprises", "comprising", "includes", "including", and "having" together with their conjugates mean "including but not limited to".

The term "consisting of" has the same meaning as "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

In discussion of the various figures described herein below, like numbers refer to like parts. In some cases, pluralities of similar or identical elements are marked with same numbers followed by letters, in some cases; same number without the letter refers to any of these elements. The drawings are generally not to scale. For clarity, non-essential elements were omitted from some of the drawing.

The optical setup for endoscopes typically used in the prior art requires a relatively large overall optical length (total optical track) of the entire optical system, which is disadvantageous for endoscopes, in particular those used as colonoscopes and gastroscopes, particularly if used in endoscopes having side-viewing camera or cameras, such as endoscopes according to embodiments of the present invention.

In addition, in sensors (such as CCD sensors) used in endoscopes of the prior art, the pixels are partially covered by a photo-shielding film, so that the light energy is concentrated in the center of the pixel, where there is a "window" in the photo-shielding film. This improves the signal-to-noise ratio and increases the light utilization efficiency. However, this also causes the sensor to be sensitive to incident angles between the light rays which have passed the micro-lenses of the sensor and the optical axis of the system. Thus, light rays having relatively small incident angles may reach the pixel, while light rays having relatively large incident angles (between the light rays which have passed the micro-lenses of the sensor and the optical axis of the system) may not reach the "window" and thus the pixel, leading to significant energy losses. The losses are maximized at the edges of the field of view, i.e. for light rays having incident angles close to that of the chief ray.

There is thus provided herein, according to some embodiments, a lens system (assembly) configured for use in an endoscope, such as colonoscope, particularly for use in a multi-sensor endoscope/colonoscope. The lens system, (optionally together with the sensor) according to some embodiments of the invention, has a short total optical length (track), for example, 5 mm or less. The lens system, according to some embodiments of the invention, is configured to provide a large incident angle, for example, a chief incident angle (for example the incident angles forming by rays $R_6$ in FIGS. 4a-4c) larger than 20°, larger than 25°, larger than 30° or between about 20-40°. The lens system, according to some embodiments of the invention provides minimal distortion (for example, less than 80%).

According to some embodiments, the sensor which is used together with the lens system, is configured to have a window in the photo-shielding film configured to allow rays having large incident angle (for example, a chief incident angle larger than 20°, larger than 25°, larger than 30° or between about 20-40°) to reach the pixel and thus improve the distortion. According to some embodiments, the width of the window (or any other dimensional parameter) may be about 30-60% of the width of the corresponding pixel. According to some embodiments, the micro-lenses of the sensor may be configured to provide substantially aplanatic conditions. In other words, the sensor may be configured to provide an image substantially free of aberrations.

FIG. 1a schematically depicts an external isometric view of an endoscope (for example, a colonoscope) 200 having multiple fields of view according to an exemplary embodiment of the current invention.

According to an exemplary embodiment of the current invention, head 230 of endoscope 200 comprises at least a forwards looking camera (such as a TV camera) and at least one side looking camera (such as a TV camera).

FIG. 1a shows front camera element 236 of forwards looking camera 116 (seen in FIG. 2c) on the front face 320 of head 230. The term "camera element" may generally refer to a camera and the optical system/assembly related to the camera. Optical axis of forwards looking camera 116 (seen for example in FIG. 2a) is substantially directed along the long dimension of the endoscope. However, since forwards looking camera 116 is typically a wide angle camera, its Field of View (FOV) may include viewing directions at large angles to its optical axis. Additionally, optical windows 242a and 242b of discrete light sources such as Light Emitting Diodes (LEDs) 240a and 240b are also seen on front face 320 of head 230. It should be noted that number of LEDs used for illumination of the FOV may vary. Distal opening 340 of working channel 262 (seen for example in FIG. 2d) may preferably be located on front face 320 of head 230, such that a surgical tool inserted through working channel 262 and deployed beyond front face 320 may be viewed by forwards looking camera 116.

Distal opening 344 of a fluid channel may preferably also be located on front face 320 of head 230. The fluid channel leading to distal opening 344 may be used as a jet channel for cleaning the colon.

Liquid injector 346 having a nozzle 348 aimed at front camera element 236 is used for injecting fluid to wash contaminants such as blood, feces and other debris from front camera element 236 of forwards looking camera. Optionally the same injector is used for cleaning both front camera element 236 and one or both optical windows 242a and 242b. Injector 346 may receive fluid (for example, water and/or gas) from the fluid channel or may be fed by a dedicated cleaning fluid channel.

Figure 2A:
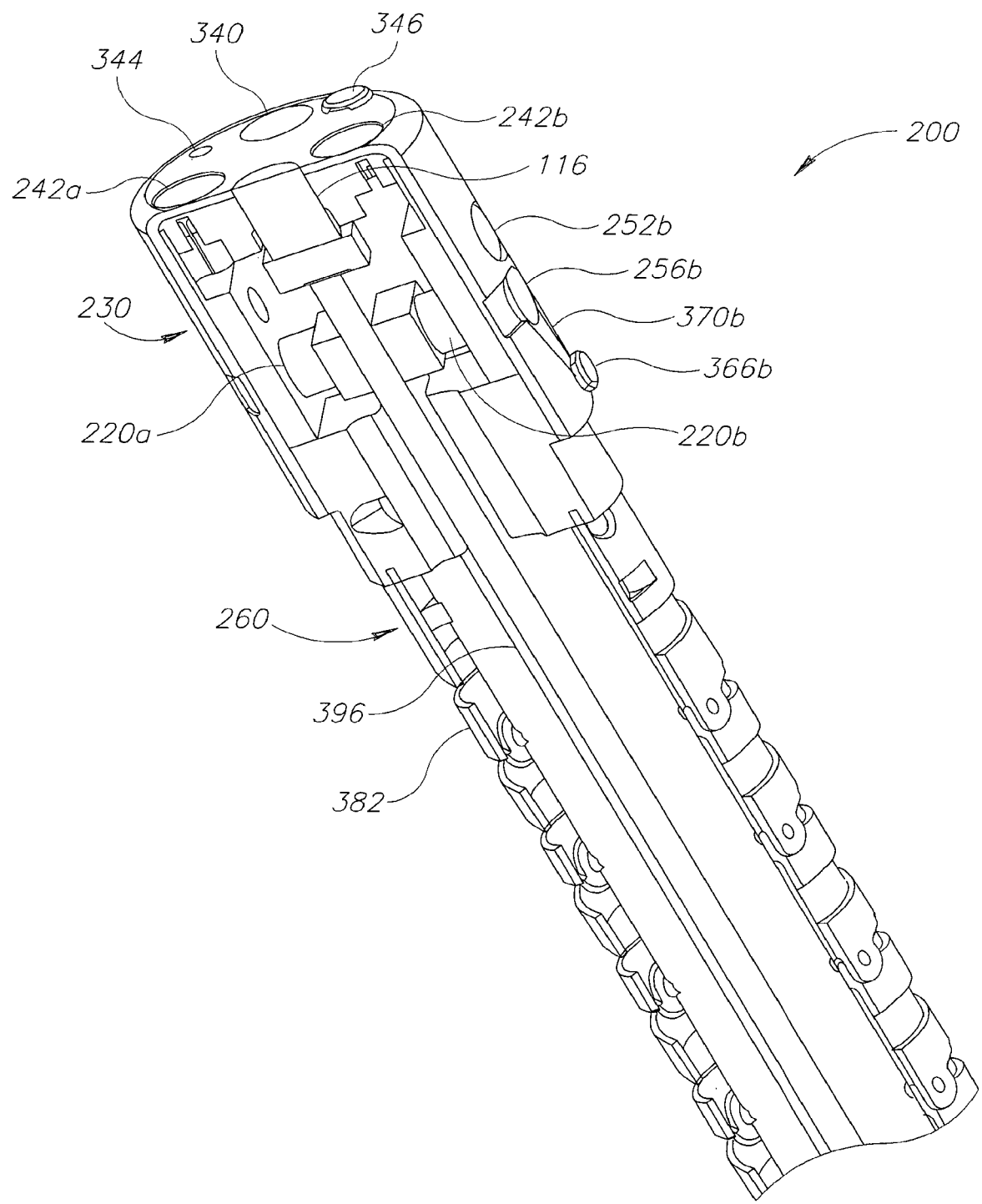
FIG. 2a schematically depicts a cross section of an endoscope having multiple fields of view, for use within bodily cavity according to an exemplary embodiment of the current invention.

Visible on the side wall 362 of head 230 is the front camera element 256 of side looking camera 220 (two such cameras are seen in FIG. 2a) and optical window 252 of a discrete light sources such as LED 250. It is noted that the number of the discrete light sources may vary. Optical axis of side looking camera 220 may be substantially directed perpendicular to the long dimension of the endoscope. However, since side looking camera 220 is typically a wide angle camera, its field of view may include viewing directions at large angles to its optical axis.

Liquid injector 366 having a nozzle 368 aimed at front looking camera element 256 is used for injecting fluid to wash contaminants such as blood, feces and other debris from front camera element 256 of side looking camera. Optionally the same injector is used for cleaning both front camera element 256 and optical windows 252. Preferably, injectors 346 and 366 are fed from same channel. An optional groove 370 helps directing the cleaning fluid from nozzle 368 towards front camera element 256. Groove 370 may be beneficial when side wall 362 is near or pressed against the rectal wall. Optionally, injector 366 may be at least partially recessed in groove 370, thus reducing the maximum diameter of head 230 and reduce the risk of injury to the rectal wall due to friction with injector 366.

In the depicted embodiment, flexible shaft 260 is constructed of a plurality of links 382 connected to each other by pivots 384. Links 382 allows pushing, pulling and rotating the endoscope while pivots 384 provide limited flexibility. The shaft is preferably covered with an elastic sheath (removed for clarity in this figure). The lumen in links 382 holds the working channel 262. Not seen in this figure are the fluid channel connected to opening 344, optional cleaning fluid channel and electrical cables supplying power to the LEDs and cameras and transmitting video signals from the camera. Generally, the shaft may also comprise mechanical actuators (not seen), for example cables attached to the links for directing and aiming the head during use.

It should be noted that while only one side looking camera is seen in FIG. 1a, optionally, according to some embodiments, two or more side looking cameras may be located within head 230. When two side looking cameras are used, the side looking cameras are preferably installed such that their field of views are substantially opposing. According to some embodiments, Different configurations and number of side looking cameras are possible and covered within the general scope of the current invention.

Figure 1B:
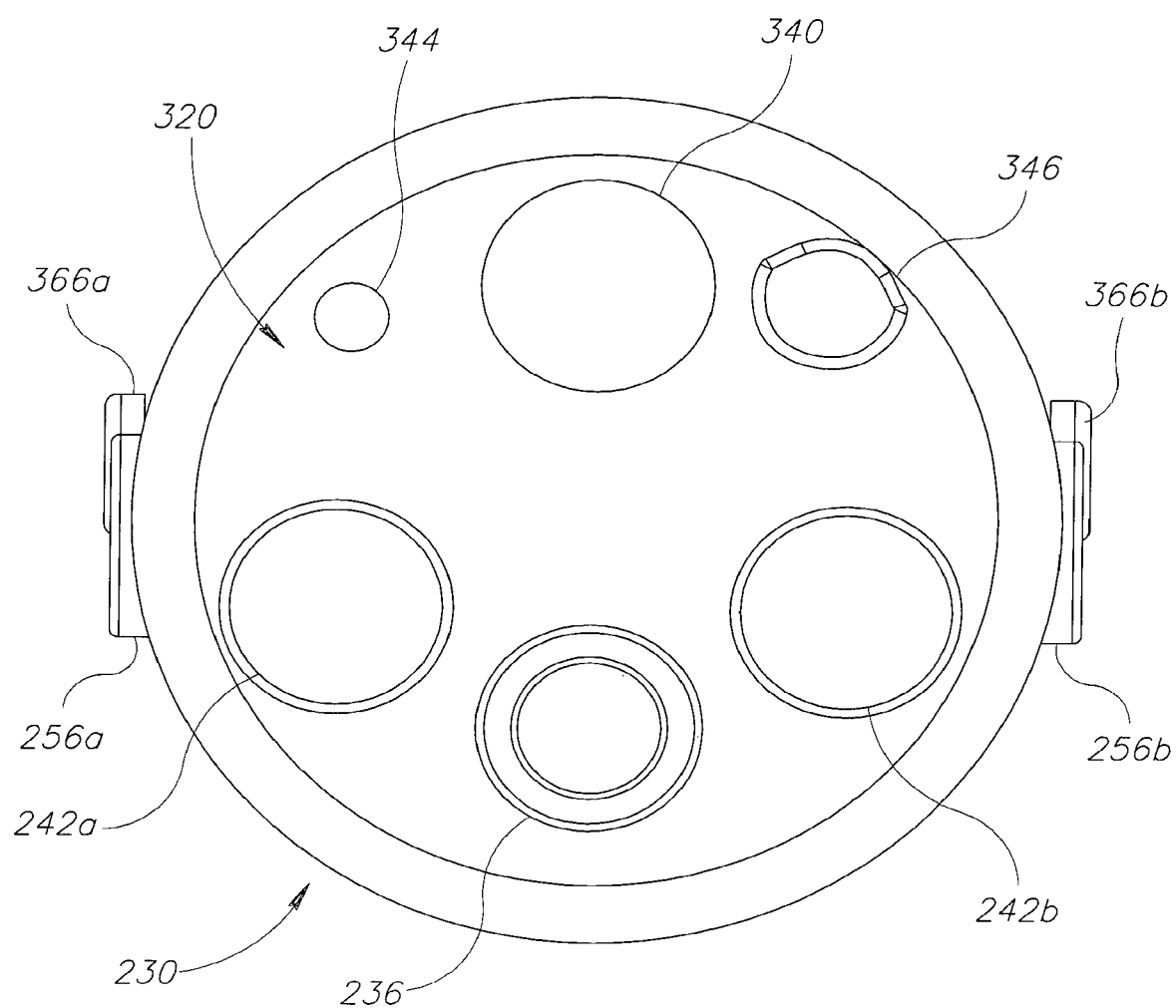
FIG. 1b schematically depicts a front view of an endoscope having multiple fields of view according to an exemplary embodiment of the current invention.

FIG. 1b schematically depicts a front view of head 230 of endoscope 200 having multiple fields of view according to an exemplary embodiment of the current invention.

Figure 2B:
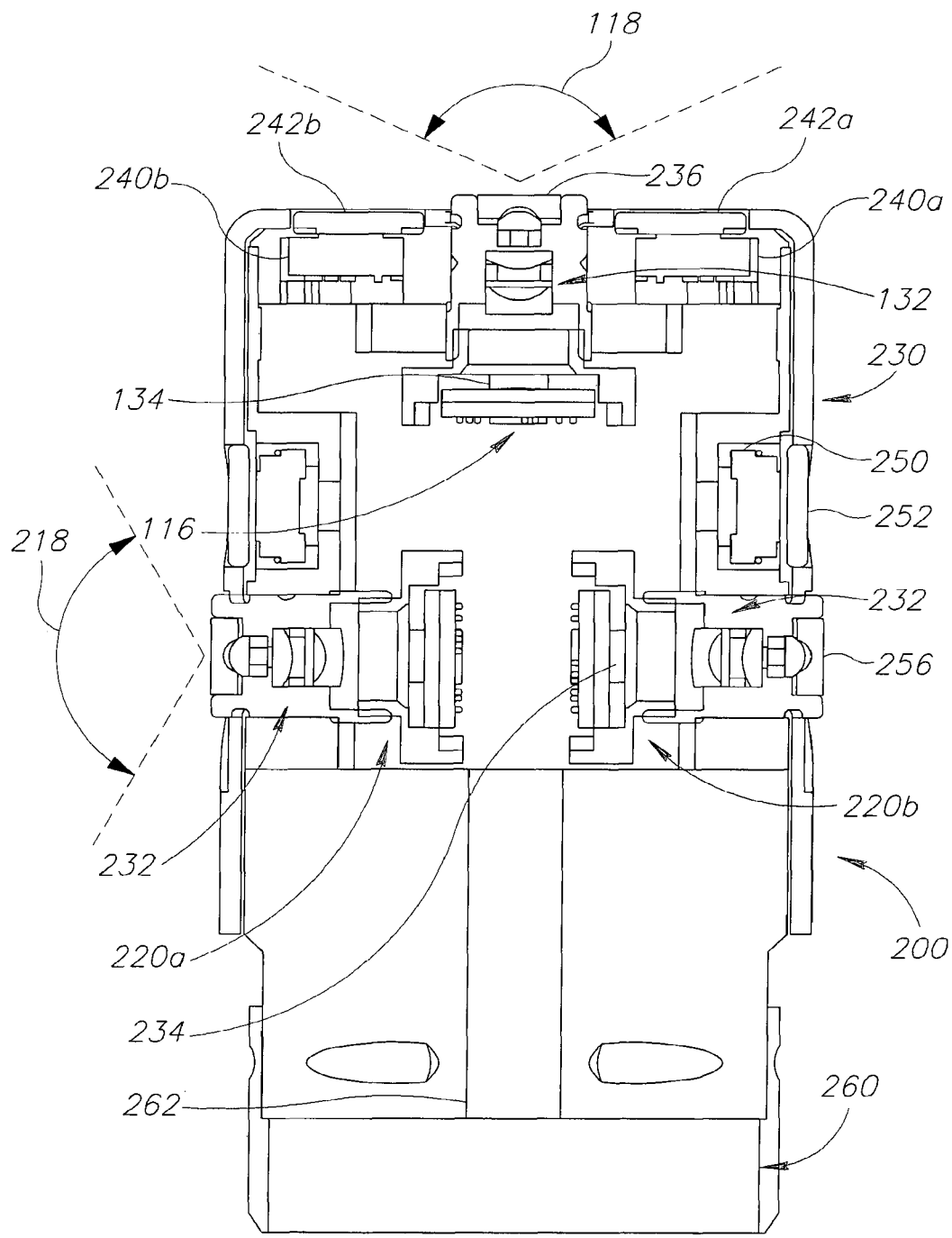
FIG. 2b schematically depicts a cross section of an endoscope front head having multiple fields of view showing some details of the head according to an exemplary embodiment of the current invention.

According to an exemplary embodiment of the current invention, head 230 of endoscope 200 comprises at least a forwards looking camera and at least one side looking camera. FIG. 2b shows a front camera element 236 of forwards looking camera 116 on the front face 320 of head 230. Additionally, optical windows 242a and 242b of LEDs 240a and 240b are also seen on front face 320 of head 230. Distal opening 340 of working channel and distal opening 344 of a fluid channel are preferably also located on front face 320 of head 230. Liquid injector 346 having a nozzle 348 is also visible in this view.

Additionally, Liquid injectors 366a and 366b aimed at side looking camera element 256a and 256b respectively are used for injecting fluid to wash contaminants such as blood, feces and other debris from front camera element 256 of side looking cameras.

Figure 1C:
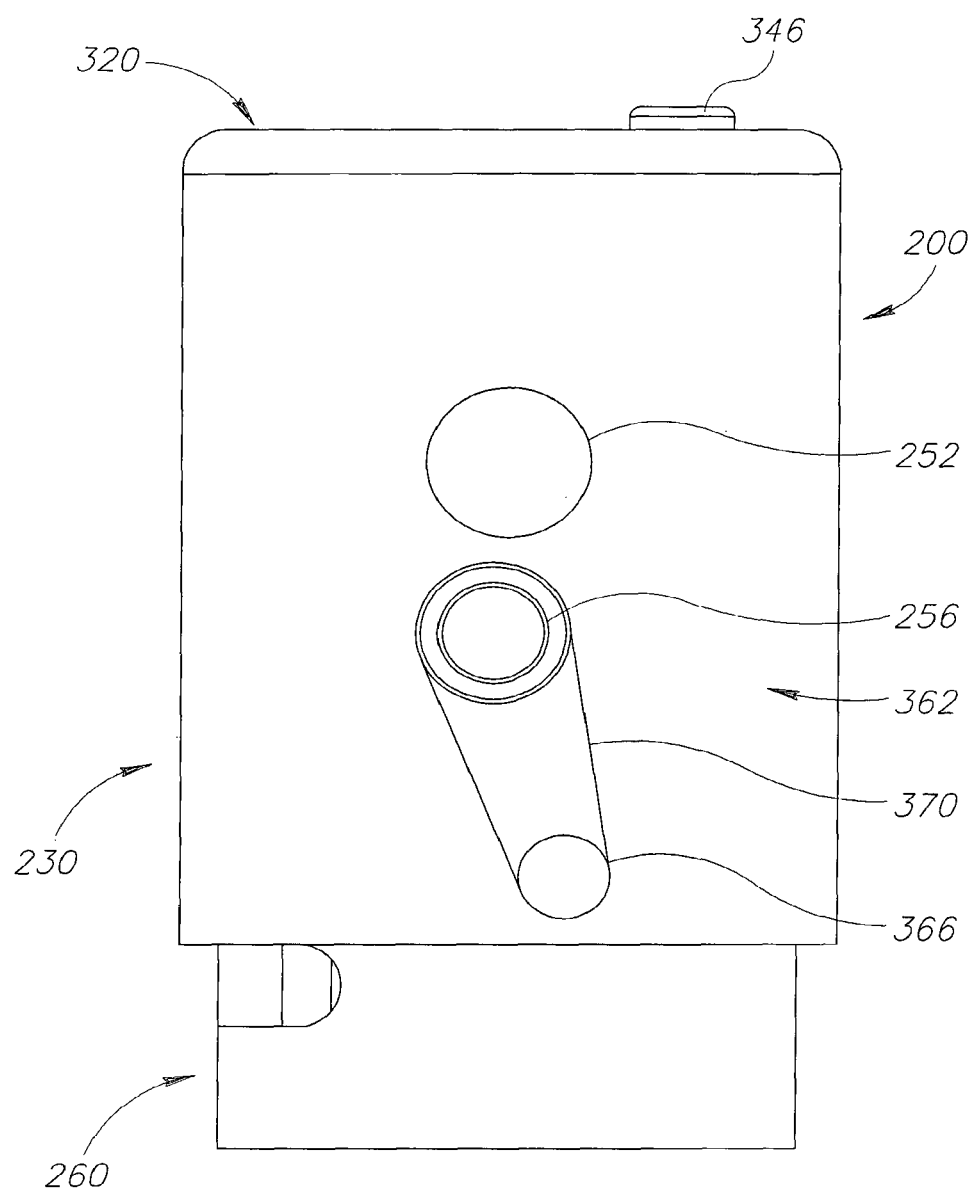
FIG. 1c schematically depicts a side view of endoscope having multiple fields of view according to an exemplary embodiment of the current invention.

FIG. 1c schematically depicts a side view of endoscope 200 having multiple fields of view according to an exemplary embodiment of the current invention.

FIG. 1c shows front camera element 256 of side looking camera 220, groove 370 and optical window 252 on the side wall 362 of head 230. Liquid injectors 346 and 366 are also visible in this view.

FIG. 2a schematically depicts a cutout isometric view of an endoscope 400 having multiple fields of view according to another exemplary embodiment of the current invention.

According to an exemplary embodiment of the current invention, head 230 of endoscope 200 comprises at least a forwards looking camera 116 and two side looking cameras 220a and 220b.

Optical windows 242a and 242b of LEDs used for forward illumination are also seen on front face of head 230.

Distal opening 340 of working channel is preferably located on front face of head 230 such that a surgical tool inserted through the working channel 262 and deployed beyond front face may be viewed by forwards looking camera 116.

Distal opening 344 of a fluid channel is preferably also located on front face of head 230. The fluid channel leading to distal opening 344 may be used as a jet channel for cleaning the colon.

Liquid injector 346 having a nozzle aimed at front camera element of camera 116 is used for injecting fluid to wash contaminants such as blood, feces and other debris from front camera element of forwards looking camera 116. Optionally the same injector is used for cleaning the front camera element and one or both optical windows 242a and 242b. Injector 346 may receive fluid from the fluid channel or may be fed by a dedicated cleaning fluid channel.

Visible on right hand side of head 230 is the front camera element 256b of side looking camera 220b and optical window 252b of side illuminating LED.

Liquid injector 366b having a nozzle aimed at front camera element 256b is used for injecting fluid to wash contaminants such as blood, feces and other debris from front camera element 256b of side looking camera 220b. Optionally the same injector is used for cleaning both front camera element 256b and optical windows 252b. An optional groove 370b helps directing the cleaning jet from injector 366b towards front camera element 256b.

Although not seen in this figure, it is understood that equivalent elements 366a, 370a, 256a and 252a are present on the left hand side of head 230.

Preferably, all the injectors 346 and 366 are fed from same channel.

In the depicted embodiment, flexible shaft 260 is constructed of a plurality of links 382 (only one is marked for clarity). Electrical cable 396 within shaft 260 is seen connected to cameras 116, 220a and 220b. The same or separate electrical cable is used to power the LEDs.

FIG. 2b schematically depicts a cross section of an endoscope 200 having multiple fields of view showing some details of the head 230 according to an exemplary embodiment of the current invention.

According to the current invention, head 230 of endoscope 200 comprises at least a forwards looking camera 116 and two side looking cameras 220a and 220b. Each of cameras 116 and 220 is provided with an optical imaging system such as lens assemblies (systems) 132 and 232 respectively and solid state detector arrays 134 and 234 respectively. Front camera elements 236 and 256 of cameras 116 and 220 respectively may be a flat protective window, but optionally an optical element used as part of the imaging systems such as solid state detector arrays 134 and 234 respectively. Optionally, cameras 116 and 220 are similar or identical, however different camera designs may be used, for example, field of views 118 and 218 may be different. Additionally or alternatively, other camera parameters such as: resolution, light sensitivity, pixel size and pixel number, focal length, focal distance and depth of field may be selected to be same or different.

Light is provided by Light Emitting Diodes (LED) that illuminates the field of views. According to some embodiments, white light LEDs may be used. According to other embodiments, other colors of LEDs or any combination of LEDs may be used (for example, red, green, blue, infrared, ultraviolet).

In the depicted embodiment, field of view 118 of forwards looking camera 116 is illuminated by two LEDs 240a and 240b located within the endoscope head 230 and protected by optical window 242a and 242b respectively.

Similarly, in the depicted embodiment, field of views of side looking camera 220 is illuminated by a single LED 250 located within the endoscope head 230 and protected by optical window 252. It should be noted that number of LED light sources and their position in respect to the cameras may vary within the scope of the current invention. For example few LEDs may be positioned behind the same protective window, a camera and an LED or plurality of LED may be located behind the same protective window, etc.

Head 230 of endoscope 200 is located at the distal end of a flexible shaft 260. Similarly to shafts of the art, shaft 260 comprises a working channel 262 for insertion of surgical tools. Additionally, shaft 260 may comprises channels for irrigation, insufflation, suction and supplying liquid for washing the colon wall.

Figure 2C:
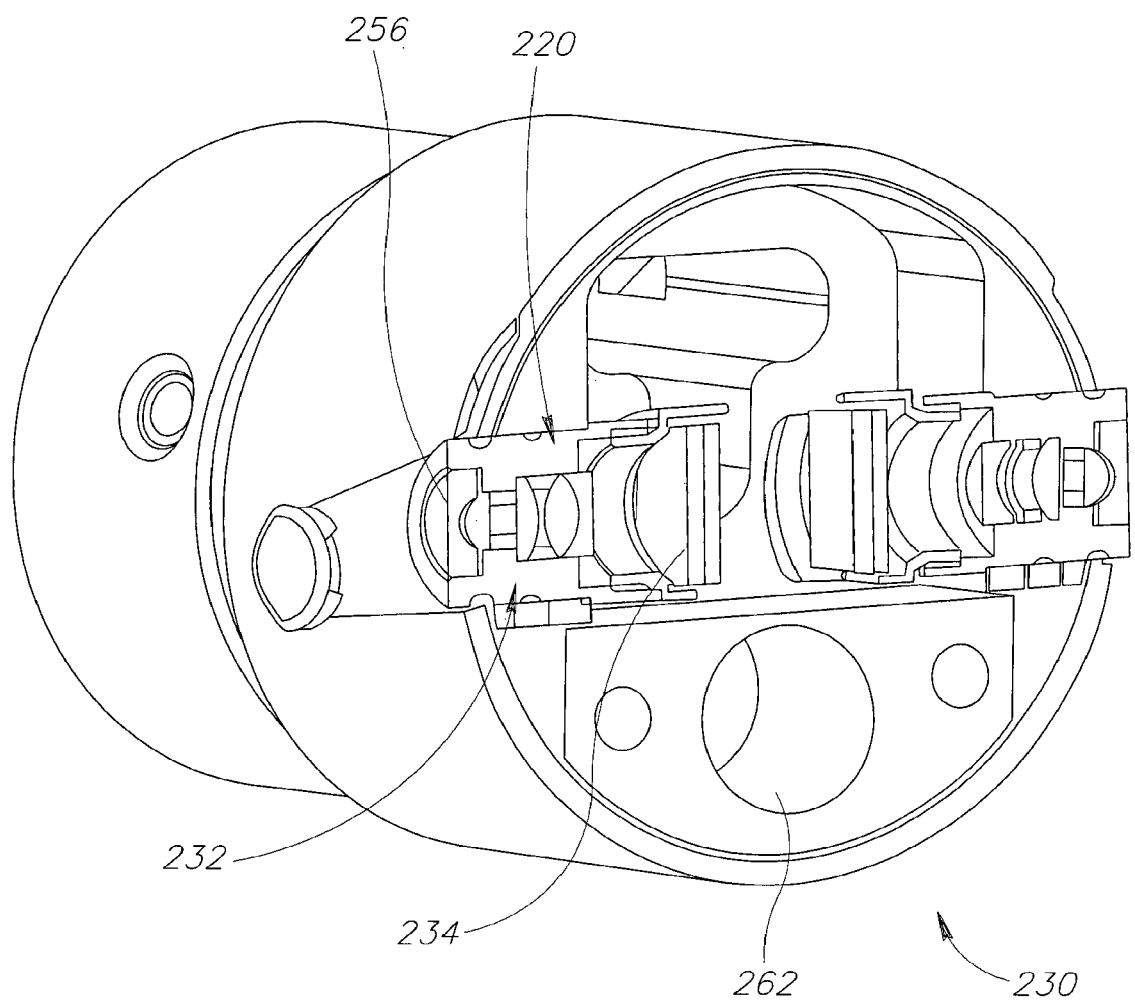
FIG. 2c schematically depicts a cutout isometric view of an endoscope having multiple fields of view according to another exemplary embodiment of the current invention.

FIG. 2c schematically depicts a cross section cutout of an endoscope 200 showing some details of the head 230 according to an exemplary embodiment of the current invention. For simplicity, details of one of the two side looking cameras are marked in the figure.

According to the current invention, head 230 of endoscope 200 comprises at least one side looking camera 220. Each of cameras 220 is provided with an optical imaging system such as lens assemblies 232 and solid state detector arrays 234. Front camera element 256 of camera 220 may be a flat protective window or an optical element used as part of the imaging system 232.

Figure 2D:
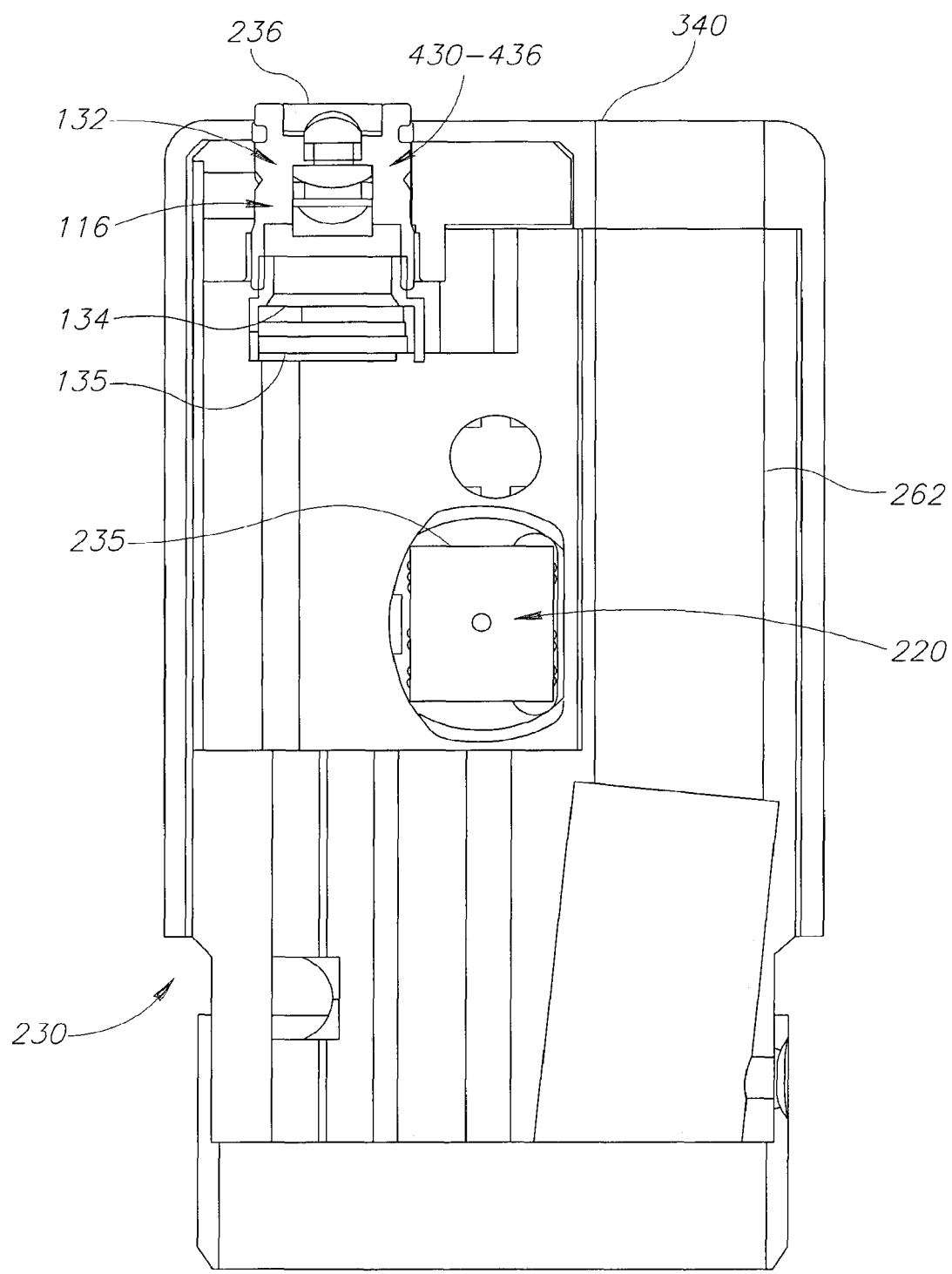
FIG. 2d schematically depicts another cutout isometric view of an endoscope having multiple fields of view according to an exemplary embodiment of the current invention.

FIG. 2d schematically depicts a cross section of an endoscope 200 having multiple fields of view showing some details of the head 230 according to an exemplary embodiment of the current invention.

According to some embodiments of the current invention, the interior of the head 230 comprises forward looking and side looking cameras 116 and 220, respectively. Cameras 116 and/or 220 comprise lens assemblies 132 and 232 (not shown), respectively, having a plurality of lenses 430 to 434 and protective glass 436 (not shown) and a solid state detector arrays 134 and 234 (not shown) connected to a printed circuit board 135 and 235 (not shown) respectively. It is noted that cameras 116 and 220 or any element related to them (such as lens assemblies 132 and 232, lenses 430 to 434 and protective glass 436, solid state detector arrays 134 and 234 and/or printed circuit board 135 and 235) may be the same or different. In other words the front looking camera and the side looking camera(s) may be the same or different in any one or any combinations of their components or other element related to them (such as optical elements).

Figure 3:
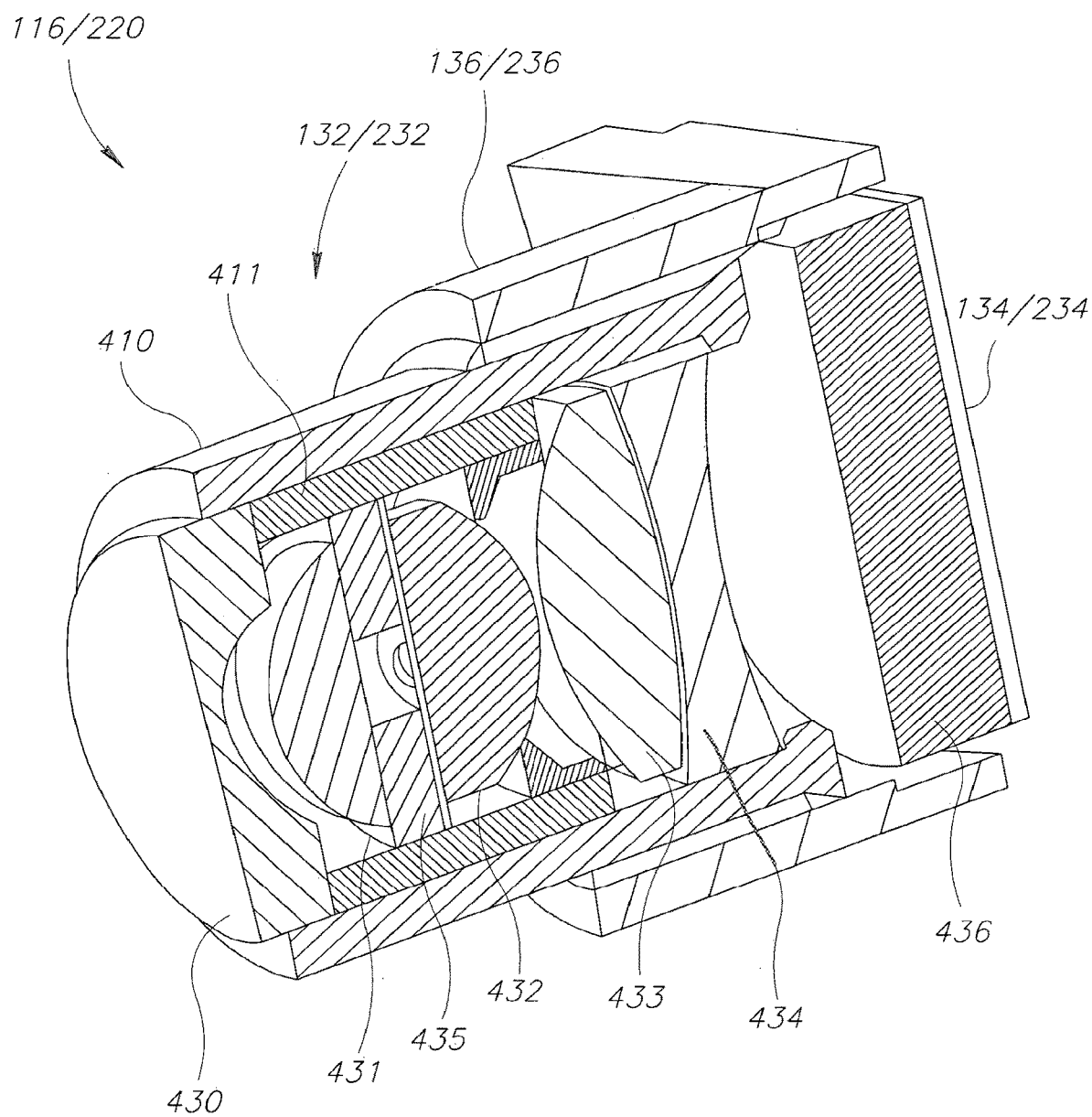
FIG. 3 schematically depicts a cross section of a lens assembly of a camera head, according to an exemplary embodiment of the current invention.

FIG. 3 schematically depicts a cross section of cameras 116 or 220, showing some details of lens assemblies 132 and 232 according to an exemplary embodiment of the current invention. It should be noted that according to some embodiments of the invention, cameras 116 and 220 may be similar or different. Optionally, the focusing distance of camera 116 is slightly different than that of camera 220. Differences in focusing distances may be achieved, for example, by (slightly) changing the distance between the lenses that comprise the lens assemblies 132 and/or 232, or between the lens assembly and the detector array.

Air gap "S" between lenses 431 and 432 acts as a stop. Air gap S may affect the focal range (the distance between the closest object and farther objects that can be imaged without excessive blurring caused by being out of optimal focusing of the lens system).

According to an exemplary embodiment of the current invention, cameras 116 and 220 comprise lens assemblies 132 and 232 respectively. The lens assemblies comprise a set of lenses 430 to 434 and protective glass 436.

Lenses 430 to 434 are situated within a (optionally metallic) barrel 410 and connector thereto (for example, glued in barrel 410). Any one of lens assemblies 132 and/or 232 may also include an adapter 411, optionally, as shown in FIG. 3, positioned within barrel 410. Adapter 411 is configured to adjust the location of one or more of the lenses and adjust the distance between lenses. Adapter 411 may also be configured to function as a stop (in this case, between lenses 432 and 433. Protective glass 436 is situated in proximity to the solid state detector arrays 134 or 234 and is optionally attached thereto.

Focal distance (the distance to the object to be optimally focused by the lens system) may be changed by changing the distance between lenses 434 and protective glass 436. As lens 434 is fixed to the barrel, and protective glass 436 is fixed to lens holder 136 (236), this distance may be varied by changing the relative positioning of lens holder 136 (236) with respect to barrel 410. The space between the lenses 434 and protective glass 436 may be an empty space or may be filled with glass or other transparent material, or a tubular spacer may be inserted to guarantee the correct distance between these lenses. Optionally, optical filters may be placed within the space. Cameras 116 and 220 further comprise solid state detector arrays 134 and 234 respectively. Solid state detector arrays 134 and 234 may each be connected to printed circuit boards. An electrical cabling may connect the printed boards to a central control system unit of the endoscope.

Solid state detector arrays 134 and 234 are attached to lens holders 136 and 236 respectively. Lens holder 136 or 236 are attached to lens assemblies 132 or 232 respectively by attaching detector array cover to barrel 410.

In some applications, protective glass 436 may be a flat-flat optical element, acting primarily as a protection of the detector array (such as detector arrays 134 and 234), and may optionally be supplied with the array. However, optical properties of protective glass 436 need to be accounted for in the optical design.

In order to assemble lens assemblies 132 or 232, lens 430 may first be inserted from left, then 431, and 432 from right. Lenses 433 and 434 which may be glued together (or separated for example by air) are then inserted from right. The complete set is now assembled in a barrel. The assembled detector (such as detector arrays 134 and 234), protective glass 436 and cover 136(236) are then added.

Figure 4A:
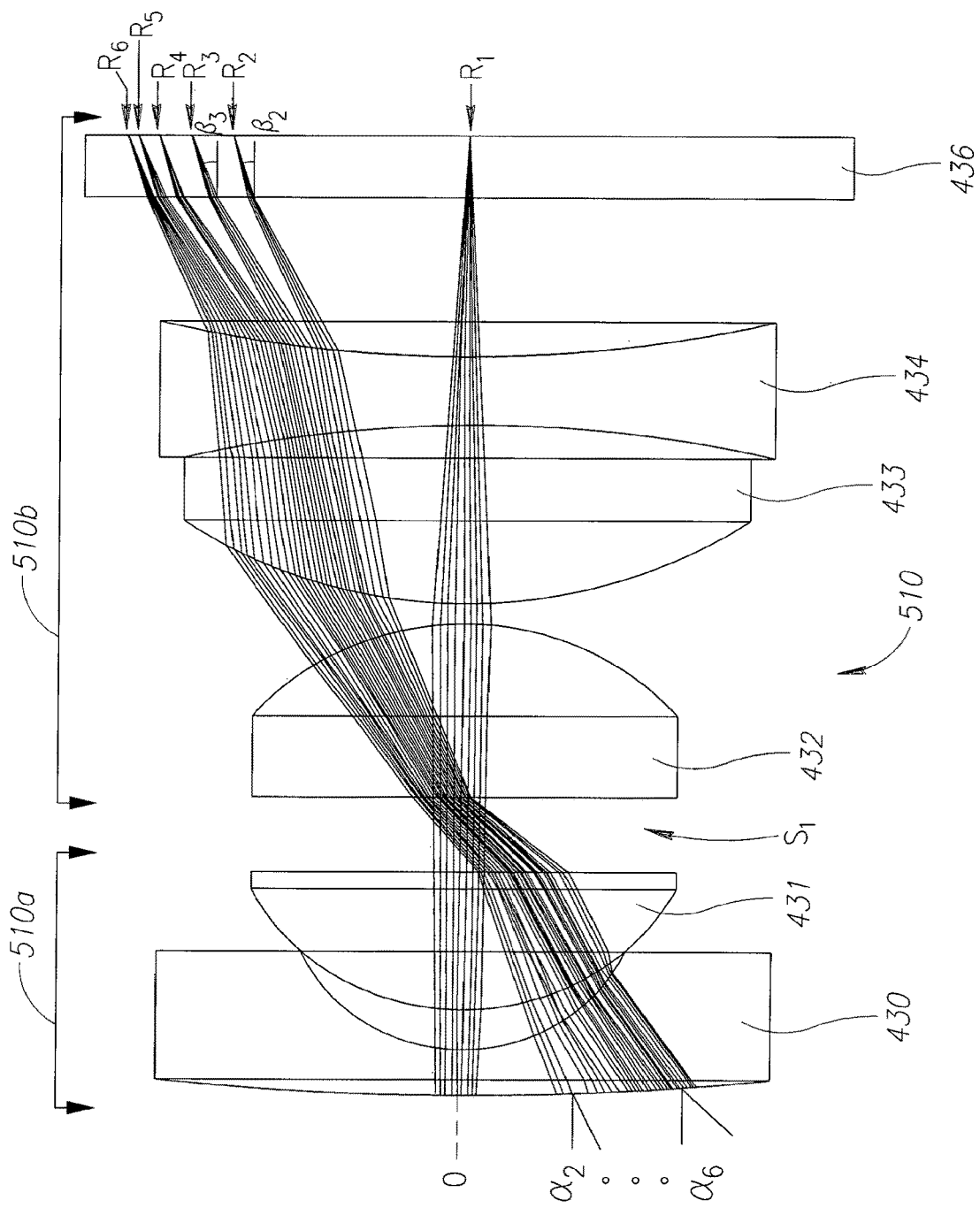
FIG. 4a schematically illustrates example of light propagation within an objective lens systems according to an exemplary embodiment of the current invention.
Figure 4B:
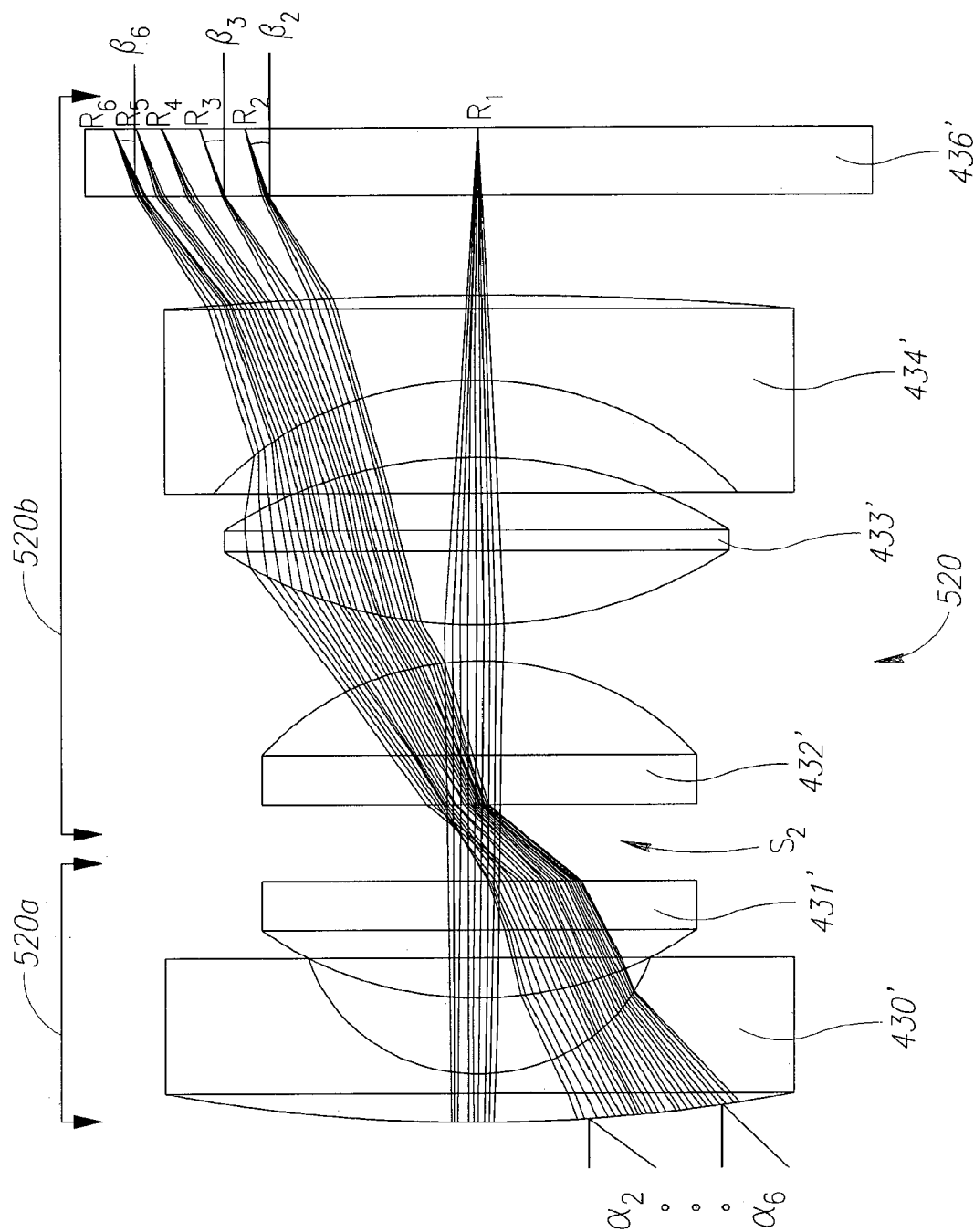
FIG. 4b schematically illustrates another example of light propagation within an objective lens system according to an exemplary embodiment of the current invention.
Figure 4C:
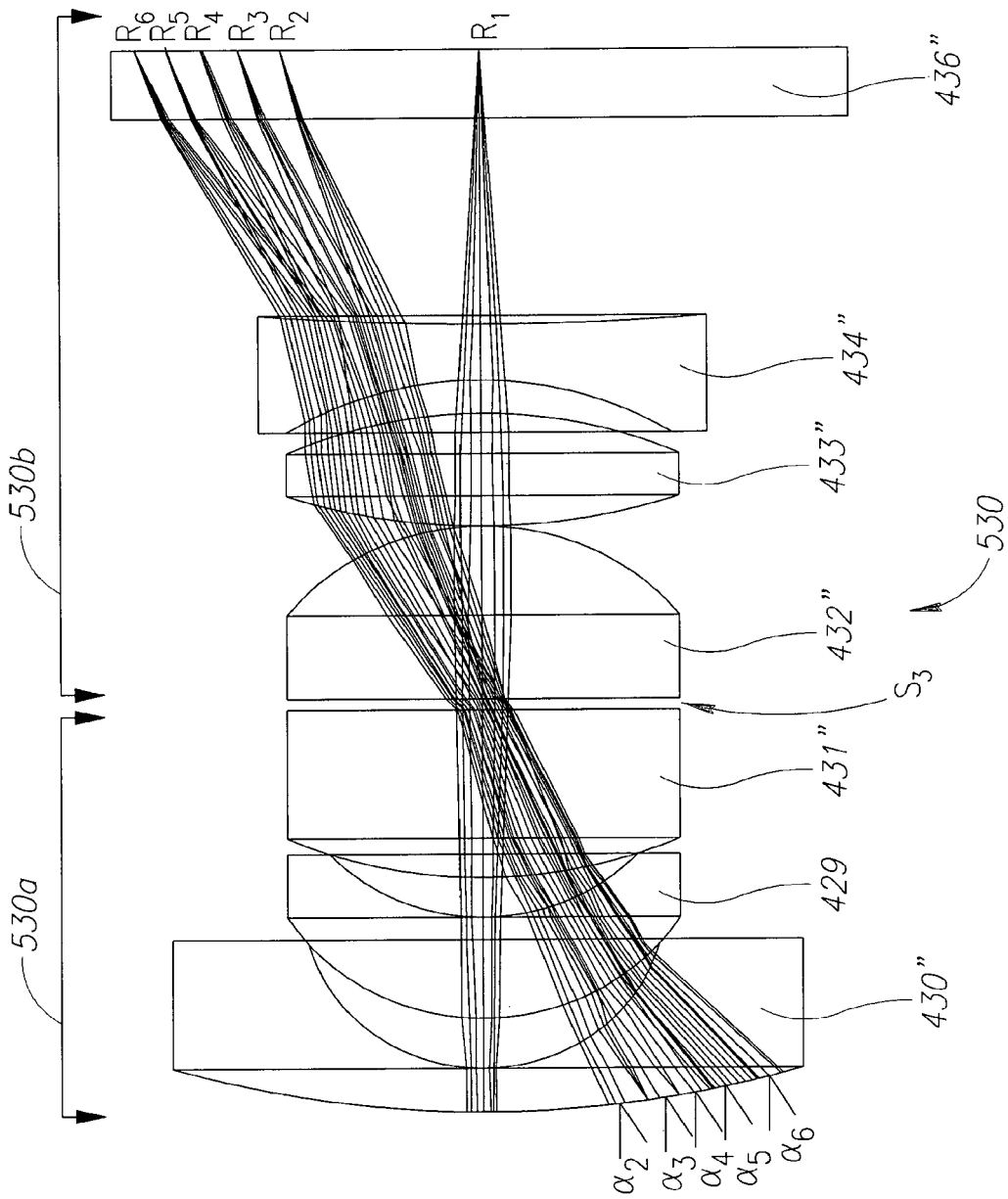
FIG. 4c schematically illustrates another example of light propagation within an objective lens system according to an exemplary embodiment of the current invention.

FIGS. 4*a*, 4*b* and 4*c* illustrate three examples for the lens assemblies such as lens assemblies 132 and 232 according to the present invention, having objective lens systems 510, 520 and 530 respectively. The sensor used in the lens assemblies 132 and 232, according to this exemplary embodiment, may be a Charge Coupled Device sensor (CCD) having an array of micro-lenses but other sensors, such as CMOS, may also be used.

In an exemplary embodiment of the invention, a color CCD camera having resolution of approximately 800×600 pixels were used with total active area of approximately 3.3×2.95 mm. The optical resolution of the lens, according to exemplary embodiments of the current invention, was designed to match the resolution of the sensor. The objective lens system 510 (520/530) are preferably corrected for chromatic; spherical and astigmatism aberrations. In an exemplary embodiment of the invention, objective lens system 510 (520/530) is approximately 4.60 mm (4.62) total length, measured from front face of front lens to the front surface of the sensor. In an exemplary embodiment of the invention, objective lens systems 510 and 520 are wide angle objectives having approximately 170 degrees acceptance angle. In an exemplary embodiment of the invention, objective lens system 510 (520/530) has a short focal distance of measured from the front surface of the front lens to the imaged object. In an exemplary embodiment of the invention objective lens system 510 (520/530) has Depth of Focus (DOF) allowing to effectively image objects between 4-110 mm (or between, 3.5-50 mm). In an exemplary embodiment of the invention, objective lens system 510, 520 and 530 has maximum diameter of about 2.5 mm, defined by the diameter of the front lens, and is housed in a barrel having maximum outer diameter of approximately 3.6 mm. It should be noted that other design parameters may be selected within the general scope of the current invention.

The objective lens system 510 (520/530) has an optical axis "0" depicted by the dashed line. The lens system comprises a front sub-system 510*a* (520*a*/530*a*) and a rear sub-system 510*b* (520*b*/530*b*).

Front sub-system 510*a* (520*a*) (FIG. 4*a* (4*b*)) comprises a front lens 430 (430') located closest to the object to be viewed, having a negative power and lens 431(431') having a positive power.

Front lens 430 (430') is oriented with its concave surface facing toward the optical image formed and away from the object to be viewed and optionally having a diameter substantially greater than the largest dimension of the rear sub-system 510*b* in the direction perpendicular to the optical axis. Lens 431(431') has a positive power.

Rear sub-system 510*b* (520*b*) comprises lenses 432, 433; 434; and protective glass 436 (lenses 432'; 433'; 434'; and 436'), wherein 432 (432'), has a positive power, 433 (433') has a positive power, 434 (434') has a negative power, and 436 (436') has essentially no optic power. It is noted that protective glass 436 (436') may be a part of the sensor or a part of the rear sub-system 510*b* (520*b*). Lenses 433 and 434 (433' and 434') of the rear sub-system 510*b* (520*b*) compose an achromatic sub-assembly (a compound achromatic sub-assembly as seen in FIG. 4*a*, where lenses 433 and 434 are cemented or non-compound achromatic sub-assembly as seen in FIG. 4*b*, where lens 433' and lens 434' are separated). Lens 433 (433') may be biconvex with radius of curvature of its front surface being smaller than radius of curvature of its rear surface, as indicated in Tables $T_1$, $T_2$ below.

Lens 432 of the objective lens systems 510 may have a focal length $f_{432}$ satisfying the following condition: $f_{432} \leq 1.8f$, where f is the composite focal length of the total system. Particularly, for the data indicated in Table $T_1$ $f_{432}=2.05$ and f=1.234 mm, the condition: $f_{432} \leq 1.8f$ is satisfied.

Lens 432' of the objective lens systems 520 may have a focal length $f_{432'}$ satisfying the following condition: $f_{432'} \leq 1.8f$.

Particularly, for the data indicated in Table $T_2$ $f_{432}=2.05$ and f=1.15 mm, the condition: $f_{432} \leq 1.8f$ is satisfied.

The lenses may be coated with an anti-reflection coating (AR coating) for further improving the efficiency of the lens assemblies 132 (232).

An effective aperture stop $S_1$ ($S_2$) is formed between lenses 431 and 432 (431' and 432'). Effective aperture stop $S_1$ ($S_2$) may separate between front sub-system 510a (520a) and rear sub-system 510b (520b).

Front sub-system 530a (FIG. 4c) comprises a front lens 430" located closest to the object to be viewed, having a negative power and lens 431", having a positive power. Front sub-system 530a (FIG. 4c) further comprises an additional front positive lens (such as the meniscus lens 429) disposed between the first front negative lens 430" and the second front positive lens 431".

Front lens 430" is oriented with its concave surface facing toward the optical image formed and away from the object to be viewed and optionally having a diameter substantially greater than the largest dimension of the rear sub-system 530b in the direction perpendicular to the optical axis.

Rear sub-system 530b comprises lenses 432", 433", 434"; and protective glass 436", wherein 432", has a positive power, 433" has a positive power, 434" has a negative power, and 436" has essentially no optic power. It is noted that protective glass 436" may be a part of the sensor or a part of the rear sub-system 530b. Lenses 433" and 434" compose an achromatic sub-assembly of the rear sub-system 530b and may or may not be cemented to each other. Lens 433" may be biconvex with radius of curvature of its front surface being smaller than radius of curvature of its rear surface, as indicated in Table $T_3$ below.

Lens 432" of the objective lens systems 530 may have a focal length $f_{432}$ satisfying the following condition: $f_{432"} \leq 1.8f$, where f is the composite focal length of the total system. Particularly, for the data indicated in Table $T_3$ $f_{432"}=2.26$ and $f=1.06$ mm, the condition: $f_{432"} \leq 1.8f$ is satisfied.

The lenses may be coated with an anti-reflection coating (AR coating) for further improving the efficiency of the lens assemblies 132 (232).

An effective aperture stop $S_3$ is formed between lenses 431" and 432". Effective aperture stop $S_3$ may separate between front sub-system 530a and rear sub-system 530b.

Tables $T_1$, $T_2$ and $T_3$ summarize the parameters of lenses in the objective lens systems 510, 520 and 530, respectively, according to some embodiments of the current invention:

TABLE $T_1$ (FOV = 164°, DOF = 3-110 mm, f = 1.234 mm, total optical track 4.09 mm)

| Lens | Type | $R_1$ | $R_2$ | Th | D | Glass | Semi-Diameter $d_1/2$ | Semi-Diameter $d_2/2$ | $f_{mm}$ |
|---|---|---|---|---|---|---|---|---|---|
| 430 | Negative | 15 | 0.7 | 0.2 | 0.18 | N-LASF3 | 1.2 | 0.64 | −0.837 |
| 431 | Plano-convex | 0.9 | Infinity | 0.56 | 0.27 | N-LASF3 | 0.8 | 0.8 | 1.02 |
| $S_1$ | Stop | | | | 0.05 | | 0.104 | | |
| 432 | Plano-convex | Infinity | −1.0 | 0.75 | 0.09 | FK5 | 0.8 | 0.8 | 2.05 |
| 433 | Biconvex | 1.93 | −4.2 | 0.75 | 0.005 | N-LAK22 | 1.1 | 1.1 | 2.13 |
| 434 | Biconcave | −4.2 | 4.44 | 0.3 | 0.65 | N-SF66 | 1.1 | 1.2 | −2.3 |
| 436 | Protection Glass | Infinity | Infinity | 0.3 | 0 | N-BK7 | 1.5 | 1.5 | Infinity |

TABLE $T_2$ (FOV = 164°, DOF = 3-110 mm, f = 1.15 mm, total optical track 4.09 mm)

| Lens | Type | $R_1$ | $R_2$ | Th | D | Glass | Semi-Diameter $d_1/2$ | Semi-Diameter $d_2/2$ | $f_{mm}$ |
|---|---|---|---|---|---|---|---|---|---|
| 430 | Negative | 6 | 0.7 | 0.2 | 0.3 | N-LASF3 | 1.2 | 0.66 | −0.91 |
| 431 | Plano-convex | 1.26 | Infinity | 0.50 | 0.27 | N-LASF3 | 0.8 | 0.8 | 1.43 |
| $S_1$ | Stop | | | | 0.05 | | 0.105 | | |
| 432 | Plano-convex | Infinity | −1.0 | 0.60 | 0.15 | FK5 | 0.8 | 0.8 | 2.05 |
| 433 | Biconvex | 1.67 | −1.65 | 0.70 | 0.30 | FK5 | 0.95 | 0.95 | 1.83 |
| 434 | Meniscus | −1.33 | −12.0 | 0.35 | 0.40 | N-SF66 | 1.0 | 1.2 | −1.65 |
| 436 | Protection Glass | Infinity | Infinity | 0.3 | 0 | N-BK7 | 1.5 | 1.5 | Infiniy |

Table 3, shows an example of a six-component system also comprising an additional positive lens 429 (for example, as indicated in Table 3, a meniscus lens).

TABLE $T_3$ (FOV = 164°, DOF = 3-110 mm, f = 1.06 mm, total optical track 4.69 mm)

| Lens | Type | $R_1$ | $R_2$ | Th | D | Glass | Semi-Diameter $d_1/2$ | Semi-Diameter $d_2/2$ | $f_{mm}$ |
|---|---|---|---|---|---|---|---|---|---|
| 430" | Negative | 4.3 | 0.75 | 0.2 | 0.22 | N-LASF3 | 1.3 | 0.72 | −1.06 |
| 429 | Meniscus | 0.95 | 0.9 | 0.44 | 0.18 | N-SF66 | 0.8 | 0.65 | 5.75 |
| 431" | Plano-convex | 2.0 | Infinity | 0.75 | 0.02 | N-LASF3 | 0.8 | 0.8 | 2.26 |
| $S_3$ | Stop | | | | 0.02 | | 0.116 | | |
| 432" | Plano-convex | Infinity | −1.0 | 0.78 | 0 | N-PSK57 | 0.8 | 0.8 | 1.69 |

TABLE T$_3$-continued (FOV = 164°, DOF = 3-110 mm, f = 1.06 mm, total optical track 4.69 mm)

| Lens | Type | R$_1$ | R$_2$ | Th | D | Glass | Semi-Diameter d$_1$/2 | Semi-Diameter d$_2$/2 | f$_{mm}$ |
|------|------|-------|-------|------|-------|-------|------|------|------|
| 433" | Biconvex | 2.52 | −2.0 | 0.50 | 0.154 | YGH52 | 0.8 | 0.8 | 1.49 |
| 434" | Biconcav | −1.44 | 11.0 | 0.25 | 0.91 | PBH56 | 0.8 | 0.9 | −1.50 |
| 436" | Protection Glass | Infinity | Infinity | 0.3 | 0 | N-BK7 | 1.5 | 1.5 | Infiniy |

R$_1$—radius of curvature of the lens front surface (front surface is the surface facing the direction of the object);
R$_2$—radius of curvature of the lens rear surface (facing away from the object);
Th—thickness of the lens—from center of front surface to center of rear surface;
Glass—lens glass type;
d$_1$—radius of the front optical surface of the lens;
d$_2$—radius of the rear optical surface of the lens;
D—distance between components such as lenses, measured front center of rear surface of the component, such as lens to the front surface of the next optical element (in the case of a stop, S, the distance is measured front center of rear surface of a component on the front side of the stop, to the front surface of the next component),
As commonly used, radius of curvature equal to infinity is interpreted as planar. All lenses are optionally spherical.

FIGS. 4a, 4b and 4c also show the propagation of five incident rays of light R$_1$ to R$_6$ through the objective lens system 510, 520 and 530 respectively, from the front lens 430 (FIG. 4a), 430' (FIG. 4b) or 430" (FIG. 4c) till the creating of an image of the object at an image plane.

Rays R$_1$ to R$_6$, enter the lens assembly at angles α$_1$ (alpha 1) to a$_6$ (alpha 6), respectively, for example, essentially equal to the following angles: a$_1$=0°, a$_2$=45°, a$_3$=60°, a$_4$=75° and a$_5$=84°. The corresponding incident angles (the angles between the light rays which have passed the micro-lenses of the sensor and the optical axis of the system) are □$_1$ (beta 1)-□$_6$ (beta 6). According to some embodiments, the chief incident angle (for example the incident angles forming by rays R$_6$ in FIGS. 4a-4c) is larger than 20°, larger than 25°, larger than 30° or between about 20-40°. The lens system, according to some embodiments of the invention provides minimal distortion (for example, less than 80%).

The optical system assembly 132 (232) may be assembled by a method comprising the step of:
Optionally, cementing the rear doublet of lenses 433-434 (433'-434');
and:
Assembling in the barrel the front lenses 430 (430');
Assembling lens 431 (431') in the barrel;
Assembling lens 432 (432') in the barrel;
Assembling in the barrel, the rear doublet 433-434 (433'-434'); and
Note that front lens 430 (430') may be assembled last.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. An objective lens system comprising:
a plurality of lenses;
a first sleeve having a first passage extending therethrough;
an image sensor received in the first passage; and
a second sleeve received in the first passage, wherein the second sleeve has a second passage extending therethrough, wherein the plurality of lenses are received in the second passage, and wherein the second sleeve is configured to move longitudinally within the first sleeve, without rotating about a central longitudinal axis of the first passage, to change a distance between:
(a) a lens of the plurality of lenses that is closest to the image sensor, and (b) the image sensor;
wherein the plurality of lenses include a first group of lenses, wherein the first group of lenses includes:
a first negative lens,
a first positive lens positioned on an image side of the negative lens, and
a front meniscus lens disposed between the negative lens and the positive lens; and
wherein the plurality of lenses further includes a second group of lenses separate from the first group of lenses, wherein the second group of lenses includes:
a second positive lens, and
an achromatic sub-assembly comprising:
a third positive lens, and
a second negative lens, wherein the achromatic sub-assembly is positioned on an image side of the second positive lens.

2. The objective lens system of claim 1, wherein the objective lens system has a length of 5 mm or less.

3. The objective lens system of claim 1, wherein the image sensor is directly coupled to the lens holder.

4. The objective lens system of claim 1, wherein at least two lenses of the second plurality of lenses are positioned within the lens holder.

5. The objective lens system of claim 1, further comprising a protective cover, the protective cover comprising a pane of protective glass between the plurality of lenses and the image sensor.

6. The objective lens system of claim 5, wherein the pane of protective glass is directly coupled to the lens holder.

7. The objective lens system of claim 1, wherein the image sensor is directly coupled to a proximalmost end of the lens holder.

8. The objective lens system of claim 1, wherein a distalmost lens of the plurality of lenses protrudes distally from the lens barrel.

9. The objective lens system of claim 1, wherein the first passage is defined by a radially-inward facing surface of the lens holder.

10. The objective lens system of claim 1, wherein the first passage extends from a proximal end of the lens holder to a distal end of the lens holder.

\* \* \* \* \*